(12) United States Patent
Goldin et al.

(10) Patent No.: US 8,353,911 B2
(45) Date of Patent: Jan. 15, 2013

(54) EXTENDABLE CUTTING MEMBER

(75) Inventors: Mark Goldin, Orlando, FL (US); Brian Schumacher, Orlando, FL (US)

(73) Assignee: AOI Medical, Inc., Orlando, FL (US)

( * ) Notice: Subject to any disclaimer, the term of this patent is extended or adjusted under 35 U.S.C. 154(b) by 1185 days.

(21) Appl. No.: 12/124,672

(22) Filed: May 21, 2008

(65) Prior Publication Data

US 2008/0294166 A1 Nov. 27, 2008

Related U.S. Application Data

(60) Provisional application No. 60/939,355, filed on May 21, 2007, provisional application No. 60/939,365, filed on May 21, 2007, provisional application No. 60/939,362, filed on May 21, 2007.

(51) Int. Cl.
A61B 17/32 (2006.01)
(52) U.S. Cl. .......................... 606/79; 606/170
(58) Field of Classification Search .............. 606/79–85, 606/167, 170, 171, 180; 30/162, 335; 83/651, 83/651.1
See application file for complete search history.

(56) References Cited

U.S. PATENT DOCUMENTS

| 1,685,380 A | 9/1928 | Shultz |
| 3,030,951 A | 4/1962 | Mandarino |
| 3,112,743 A | 12/1963 | Cochran et al. |
| 3,320,957 A | 5/1967 | Sokolik |
| 4,065,817 A | 1/1978 | Branemark et al. |
| 4,313,434 A | 2/1982 | Segal |
| 4,369,772 A | 1/1983 | Miller |
| 4,403,606 A | 9/1983 | Woo et al. |
| 4,403,607 A | 9/1983 | Woo et al. |
| 4,493,317 A | 1/1985 | Klaue |
| 4,494,535 A | 1/1985 | Haig |
| 4,503,848 A | 3/1985 | Caspar et al. |
| 4,513,744 A | 4/1985 | Klaue |
| 4,653,489 A | 3/1987 | Tronzo |
| 4,743,260 A | 5/1988 | Burton |
| 4,751,922 A | 6/1988 | DiPietropolo |
| 4,773,406 A | 9/1988 | Spector et al. |
| 4,794,918 A | 1/1989 | Wolter |
| 4,969,888 A | 11/1990 | Scholter et al. |
| 5,002,544 A | 3/1991 | Klaue et al. |
| 5,014,124 A | 5/1991 | Fujisawa |

(Continued)

FOREIGN PATENT DOCUMENTS

DE 39 14164 1/1991

(Continued)

OTHER PUBLICATIONS

Office Action dated Dec. 7, 2009 for U.S. Appl. No. 10/818,452.
International Search Report dated Mar. 21, 2007 for Application No. PCT/US06/044443.
International Search Report and Written Opinion dated Jun. 10, 2009 for Application No. PCT/US2008/064312.

(Continued)

*Primary Examiner* — Thomas Barrett
*Assistant Examiner* — Tracy Kamikawa
(74) *Attorney, Agent, or Firm* — Ulmer & Berne LLP

(57) ABSTRACT

Provided is a minimally invasive cavity formation instrument for forming tissue cavities. The instrument includes an end effector having an aperture through which a cutting element is laterally extended and retracted. The cutting element may be retracted for minimally invasive insertion into a tissue region and extended to form a tissue cavity. The end effector of the instrument may be articulated or rotated to facilitate cavity formation.

21 Claims, 20 Drawing Sheets

U.S. PATENT DOCUMENTS

| | | | |
|---|---|---|---|
| 5,019,078 A | 5/1991 | Perren et al. |
| 5,030,201 A | 7/1991 | Palestrant |
| 5,053,036 A | 10/1991 | Perren et al. |
| 5,062,845 A | 11/1991 | Kuslich et al. |
| 5,085,660 A | 2/1992 | Lin |
| 5,102,413 A | 4/1992 | Poddar |
| 5,108,404 A | 4/1992 | Scholten et al. |
| 5,147,361 A | 9/1992 | Ojima et al. |
| 5,151,103 A | 9/1992 | Tepic et al. |
| 5,211,651 A | 5/1993 | Reger et al. |
| 5,275,601 A | 1/1994 | Gogolewski et al. |
| 5,303,718 A | 4/1994 | Krajicek |
| 5,344,421 A | 9/1994 | Crook |
| 5,360,432 A | 11/1994 | Shturman |
| 5,364,399 A | 11/1994 | Lowery et al. |
| 5,376,100 A | 12/1994 | Lefebvre |
| 5,403,136 A | 4/1995 | Mathys |
| 5,403,317 A | 4/1995 | Bonutti |
| 5,423,850 A | 6/1995 | Berger |
| 5,431,671 A | 7/1995 | Nallakrishnan |
| 5,445,639 A | 8/1995 | Kuslich et al. |
| 5,480,400 A | 1/1996 | Berger |
| 5,490,859 A | 2/1996 | Mische et al. |
| 5,514,137 A | 5/1996 | Coutts |
| 5,527,311 A | 6/1996 | Procter et al. |
| 5,540,707 A | 7/1996 | Ressemann et al. |
| 5,549,612 A | 8/1996 | Yapp et al. |
| 5,549,679 A | 8/1996 | Kuslich |
| 5,556,429 A | 9/1996 | Felt |
| 5,562,672 A | 10/1996 | Huebner et al. |
| 5,571,189 A | 11/1996 | Kuslich |
| 5,591,170 A | 1/1997 | Spievack et al. |
| 5,607,426 A | 3/1997 | Ralph et al. |
| 5,613,967 A | 3/1997 | Engelhardt et al. |
| 5,616,144 A | 4/1997 | Yapp et al. |
| 5,658,310 A | 8/1997 | Berger |
| 5,665,110 A | 9/1997 | Chervitz et al. |
| 5,674,296 A | 10/1997 | Bryan et al. |
| 5,681,310 A | 10/1997 | Yuan et al. |
| 5,681,311 A | 10/1997 | Foley et al. |
| 5,693,011 A | 12/1997 | Onik |
| 5,695,513 A | 12/1997 | Johnson et al. |
| 5,709,686 A | 1/1998 | Talos et al. |
| 5,720,749 A | 2/1998 | Rupp |
| 5,733,287 A | 3/1998 | Tepic et al. |
| 5,735,853 A | 4/1998 | Olerud |
| 5,766,176 A | 6/1998 | Duncan |
| 5,772,662 A | 6/1998 | Chapman et al. |
| 5,800,433 A | 9/1998 | Benzel et al. |
| 5,807,396 A | 9/1998 | Raveh |
| 5,827,289 A | 10/1998 | Reiley et al. |
| 5,843,103 A | 12/1998 | Wulfman |
| 5,871,486 A | 2/1999 | Huebner et al. |
| 5,888,220 A | 3/1999 | Felt et al. |
| 5,891,145 A | 4/1999 | Morrison et al. |
| 5,904,683 A | 5/1999 | Pohndorf et al. |
| 5,925,056 A | 7/1999 | Thomas et al. |
| 5,928,239 A | 7/1999 | Mirza |
| 5,935,131 A | 8/1999 | Bonutti |
| 5,964,762 A | 10/1999 | Biedermann et al. |
| 5,972,015 A | 10/1999 | Scribner et al. |
| 5,990,194 A | 11/1999 | Dunn et al. |
| 6,017,345 A | 1/2000 | Richelsoph |
| 6,019,776 A | 2/2000 | Preissman |
| 6,022,350 A | 2/2000 | Ganem |
| 6,030,389 A | 2/2000 | Wagner et al. |
| 6,033,411 A | 3/2000 | Preissman |
| 6,048,343 A | 4/2000 | Mathis et al. |
| 6,048,346 A | 4/2000 | Reiley et al. |
| 6,066,154 A | 5/2000 | Reiley et al. |
| 6,071,284 A | 6/2000 | Fox |
| 6,083,672 A | 7/2000 | Roefs et al. |
| 6,096,054 A | 8/2000 | Wyzgala et al. |
| 6,127,597 A | 10/2000 | Beyar et al. |
| 6,139,509 A | 10/2000 | Yuan et al. |
| 6,140,452 A | 10/2000 | Felt et al. |
| 6,171,312 B1 | 1/2001 | Beaty |
| 6,210,376 B1 | 4/2001 | Grayson |
| 6,214,012 B1 | 4/2001 | Karpman et al. |
| 6,221,029 B1 | 4/2001 | Mathis et al. |
| 6,224,604 B1 | 5/2001 | Suddaby |
| 6,231,615 B1 | 5/2001 | Preissman |
| 6,235,043 B1 | 5/2001 | Reiley et al. |
| 6,238,391 B1 | 5/2001 | Olsen et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,264,659 B1 | 7/2001 | Ross et al. |
| 6,273,916 B1 | 8/2001 | Murphy |
| 6,280,456 B1 | 8/2001 | Scribner et al. |
| 6,283,971 B1 | 9/2001 | Temeles |
| 6,296,639 B1 | 10/2001 | Truckai et al. |
| 6,309,420 B1 | 10/2001 | Preissman |
| 6,348,055 B1 | 2/2002 | Preissman |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,423,083 B2 | 7/2002 | Reiley et al. |
| 6,425,887 B1 | 7/2002 | McGuckin et al. |
| 6,425,923 B1 | 7/2002 | Stalcup et al. |
| 6,440,138 B1 | 8/2002 | Reiley et al. |
| 6,447,514 B1 | 9/2002 | Stalcup et al. |
| 6,450,973 B1 | 9/2002 | Murphy |
| 6,488,667 B1 | 12/2002 | Murphy |
| 6,494,535 B2 | 12/2002 | Galbreath |
| 6,558,386 B1 | 5/2003 | Cragg |
| 6,558,390 B2 | 5/2003 | Cragg |
| 6,558,396 B1 | 5/2003 | Inoue |
| 6,565,572 B2 | 5/2003 | Chappius |
| 6,575,979 B1 | 6/2003 | Cragg |
| 6,582,439 B1 | 6/2003 | Sproul |
| 6,582,446 B1 | 6/2003 | Marchosky |
| 6,592,559 B1 | 7/2003 | Pakter et al. |
| 6,595,998 B2 | 7/2003 | Johnson et al. |
| 6,599,520 B2 | 7/2003 | Scarborough et al. |
| 6,607,544 B1 | 8/2003 | Boucher et al. |
| 6,613,018 B2 | 9/2003 | Bagga et al. |
| 6,613,054 B2 | 9/2003 | Scribner et al. |
| 6,613,089 B1 | 9/2003 | Estes et al. |
| 6,620,162 B2 | 9/2003 | Kuslich et al. |
| 6,626,903 B2 | 9/2003 | McGuckin, Jr. et al. |
| 6,632,235 B2 | 10/2003 | Weikel et al. |
| 6,641,587 B2 | 11/2003 | Scribner et al. |
| 6,645,213 B2 | 11/2003 | Sand et al. |
| 6,652,568 B1 | 11/2003 | Becker et al. |
| 6,663,647 B2 | 12/2003 | Reiley et al. |
| 6,676,663 B2 | 1/2004 | Higueras et al. |
| 6,676,664 B1 | 1/2004 | Al-Assir |
| 6,676,665 B2 * | 1/2004 | Foley et al. .................. 606/105 |
| 6,679,886 B2 | 1/2004 | Weikel et al. |
| 6,685,718 B1 | 2/2004 | Wyzgala et al. |
| 6,689,132 B2 | 2/2004 | Biscup |
| 6,699,242 B2 | 3/2004 | Heggeness |
| 6,706,069 B2 | 3/2004 | Berger |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,090 B1 | 5/2004 | Cragg et al. |
| 6,740,093 B2 | 5/2004 | Hochschuler et al. |
| 6,746,451 B2 | 6/2004 | Middleton et al. |
| 6,749,595 B1 | 6/2004 | Murphy |
| 6,752,791 B2 | 6/2004 | Murphy et al. |
| 6,752,809 B2 | 6/2004 | Larkspur |
| 6,758,855 B2 | 7/2004 | Fulton, III et al. |
| 6,758,863 B2 | 7/2004 | Estes et al. |
| 6,770,079 B2 | 8/2004 | Bhatnagar et al. |
| 6,780,191 B2 | 8/2004 | Sproul |
| 6,790,210 B1 | 9/2004 | Cragg et al. |
| 6,805,697 B1 | 10/2004 | Helm et al. |
| 6,814,734 B2 | 11/2004 | Chappuis et al. |
| 6,832,988 B2 | 12/2004 | Sproul |
| 6,843,796 B2 | 1/2005 | Harari et al. |
| 6,852,095 B1 | 2/2005 | Ray |
| 6,863,672 B2 | 3/2005 | Reiley et al. |

| Patent | Date | Inventor |
|---|---|---|
| 6,863,676 B2 * | 3/2005 | Lee et al. .................. 606/159 |
| 6,869,445 B1 | 3/2005 | Johnson |
| 6,887,246 B2 | 5/2005 | Bhatnagar et al. |
| 6,899,716 B2 | 5/2005 | Cragg |
| 6,902,547 B2 | 6/2005 | Aves et al. |
| 6,916,308 B2 | 7/2005 | Dixon et al. |
| 6,921,403 B2 | 7/2005 | Cragg et al. |
| 6,923,813 B2 | 8/2005 | Phillips et al. |
| 6,932,843 B2 | 8/2005 | Smith et al. |
| 6,939,351 B2 | 9/2005 | Eckman |
| 6,960,215 B2 | 11/2005 | Olson, Jr. et al. |
| 6,960,900 B2 | 11/2005 | Fogarty et al. |
| 6,979,341 B2 | 12/2005 | Scribner et al. |
| 6,979,352 B2 | 12/2005 | Reynolds |
| 6,981,981 B2 | 1/2006 | Reiley et al. |
| 6,984,063 B2 | 1/2006 | Barker et al. |
| 7,001,342 B2 | 2/2006 | Faciszewski |
| 7,008,433 B2 | 3/2006 | Voellmicke et al. |
| 7,014,633 B2 | 3/2006 | Cragg |
| 7,044,954 B2 | 5/2006 | Reiley et al. |
| 7,056,321 B2 | 6/2006 | Pagliuca et al. |
| 7,077,865 B2 | 7/2006 | Bao et al. |
| 7,087,058 B2 | 8/2006 | Cragg |
| 7,114,501 B2 | 10/2006 | Johnson et al. |
| 7,144,397 B2 | 12/2006 | Lambrecht et al. |
| 7,153,305 B2 | 12/2006 | Johnson et al. |
| 7,153,307 B2 | 12/2006 | Scribner et al. |
| 7,156,860 B2 | 1/2007 | Wallsten |
| 7,156,861 B2 | 1/2007 | Scribner et al. |
| 7,160,306 B2 | 1/2007 | Matsuzaki et al. |
| 7,226,481 B2 | 6/2007 | Kuslich |
| 7,234,468 B2 | 6/2007 | Johnson et al. |
| 7,238,209 B2 | 7/2007 | Matsuzaki et al. |
| 7,241,297 B2 | 7/2007 | Shaolian et al. |
| 7,241,303 B2 | 7/2007 | Reiss et al. |
| 7,252,671 B2 | 8/2007 | Scribner et al. |
| 7,252,686 B2 | 8/2007 | Carrison et al. |
| 7,295,868 B2 | 11/2007 | Bascle et al. |
| 7,295,869 B2 | 11/2007 | Bascle et al. |
| 7,309,338 B2 | 12/2007 | Cragg |
| 7,318,826 B2 | 1/2008 | Teitelbaum et al. |
| 7,326,203 B2 | 2/2008 | Papineau et al. |
| 7,329,259 B2 | 2/2008 | Cragg |
| 7,346,385 B2 | 3/2008 | Bascle et al. |
| 7,399,739 B2 | 7/2008 | Shimp |
| 7,473,256 B2 | 1/2009 | Assell et al. |
| 7,476,226 B2 | 1/2009 | Weikel et al. |
| 7,488,320 B2 | 2/2009 | Middleton |
| 7,488,337 B2 | 2/2009 | Saab et al. |
| 7,491,236 B2 | 2/2009 | Cragg et al. |
| 7,500,977 B2 | 3/2009 | Assell et al. |
| 7,510,579 B2 | 3/2009 | Preissman |
| 7,530,993 B2 | 5/2009 | Assell et al. |
| 7,534,245 B2 | 5/2009 | Chappuis |
| 7,534,256 B2 | 5/2009 | Cragg |
| 7,540,875 B2 | 6/2009 | Jessen |
| 7,544,196 B2 | 6/2009 | Bagga et al. |
| 7,547,324 B2 | 6/2009 | Cragg et al. |
| 7,553,659 B2 | 6/2009 | Brodeur et al. |
| 7,555,343 B2 | 6/2009 | Bleich |
| 7,569,056 B2 | 8/2009 | Cragg et al. |
| 7,572,263 B2 | 8/2009 | Preissman |
| 2001/0011174 A1 | 8/2001 | Reiley et al. |
| 2002/0026195 A1 | 2/2002 | Layne et al. |
| 2002/0029047 A1 | 3/2002 | Bascle et al. |
| 2002/0032444 A1 | 3/2002 | Mische |
| 2002/0058885 A1 * | 5/2002 | Burbank et al. ............... 600/567 |
| 2002/0068974 A1 | 6/2002 | Kuslich et al. |
| 2002/0116064 A1 | 8/2002 | Middleton |
| 2002/0133170 A1 * | 9/2002 | Tsuruta .................. 606/127 |
| 2002/0188300 A1 | 12/2002 | Arramon et al. |
| 2003/0009208 A1 | 1/2003 | Snyder et al. |
| 2003/0032929 A1 | 2/2003 | McGuckin |
| 2003/0032963 A1 | 2/2003 | Reiss et al. |
| 2003/0074075 A1 | 4/2003 | Thomas et al. |
| 2003/0105469 A1 | 6/2003 | Karmon |
| 2003/0130664 A1 | 7/2003 | Boucher et al. |
| 2003/0135237 A1 | 7/2003 | Cragg et al. |
| 2003/0171812 A1 | 9/2003 | Grunberg et al. |
| 2003/0191474 A1 | 10/2003 | Cragg et al. |
| 2003/0191489 A1 | 10/2003 | Reiley et al. |
| 2003/0204189 A1 | 10/2003 | Cragg |
| 2003/0220648 A1 | 11/2003 | Osorio et al. |
| 2003/0229372 A1 | 12/2003 | Reiley et al. |
| 2003/0233096 A1 | 12/2003 | Osorio et al. |
| 2004/0010263 A1 | 1/2004 | Boucher et al. |
| 2004/0019354 A1 | 1/2004 | Johnson et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0049202 A1 | 3/2004 | Berger |
| 2004/0068242 A1 | 4/2004 | McGuckin |
| 2004/0073139 A1 | 4/2004 | Hirsch et al. |
| 2004/0087956 A1 | 5/2004 | Weikel et al. |
| 2004/0097930 A1 | 5/2004 | Justis et al. |
| 2004/0098015 A1 | 5/2004 | Weikel et al. |
| 2004/0102774 A1 | 5/2004 | Trieu |
| 2004/0122438 A1 | 6/2004 | Abrams |
| 2004/0153064 A1 | 8/2004 | Foley et al. |
| 2004/0153115 A1 | 8/2004 | Reiley et al. |
| 2004/0167532 A1 | 8/2004 | Olson et al. |
| 2004/0167561 A1 | 8/2004 | Boucher et al. |
| 2004/0167562 A1 | 8/2004 | Osorio et al. |
| 2004/0210231 A1 | 10/2004 | Boucher et al. |
| 2004/0210297 A1 | 10/2004 | Lin et al. |
| 2004/0215197 A1 | 10/2004 | Smith et al. |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0267269 A1 | 12/2004 | Middleton et al. |
| 2005/0015148 A1 | 1/2005 | Jansen et al. |
| 2005/0038514 A1 | 2/2005 | Helm et al. |
| 2005/0043737 A1 | 2/2005 | Reiley et al. |
| 2005/0055097 A1 | 3/2005 | Grunberg et al. |
| 2005/0090852 A1 | 4/2005 | Layne et al. |
| 2005/0113919 A1 | 5/2005 | Cragg et al. |
| 2005/0113929 A1 | 5/2005 | Cragg et al. |
| 2005/0119662 A1 | 6/2005 | Reiley et al. |
| 2005/0124989 A1 | 6/2005 | Suddaby |
| 2005/0131267 A1 | 6/2005 | Talmadge |
| 2005/0131268 A1 | 6/2005 | Talmadge |
| 2005/0137601 A1 | 6/2005 | Assell et al. |
| 2005/0137604 A1 | 6/2005 | Assell et al. |
| 2005/0137605 A1 | 6/2005 | Assell et al. |
| 2005/0137607 A1 | 6/2005 | Assell et al. |
| 2005/0149049 A1 | 7/2005 | Assell et al. |
| 2005/0165406 A1 | 7/2005 | Assell et al. |
| 2005/0182339 A1 * | 8/2005 | Lee et al. .................. 600/564 |
| 2005/0182417 A1 | 8/2005 | Pagano |
| 2005/0187556 A1 | 8/2005 | Stack et al. |
| 2005/0203527 A1 | 9/2005 | Carrison et al. |
| 2005/0261695 A1 | 11/2005 | Cragg et al. |
| 2006/0004369 A1 | 1/2006 | Patel et al. |
| 2006/0116689 A1 | 6/2006 | Albans et al. |
| 2006/0116690 A1 | 6/2006 | Pagano |
| 2006/0142795 A1 | 6/2006 | Nguyen et al. |
| 2006/0149268 A1 | 7/2006 | Truckai et al. |
| 2006/0155289 A1 | 7/2006 | Windhager et al. |
| 2006/0235451 A1 | 10/2006 | Schomer et al. |
| 2007/0027464 A1 | 2/2007 | Way et al. |
| 2007/0055259 A1 | 3/2007 | Norton et al. |
| 2007/0123877 A1 | 5/2007 | Goldin et al. |
| 2008/0114364 A1 | 5/2008 | Goldin et al. |

FOREIGN PATENT DOCUMENTS

| | | |
|---|---|---|
| EP | 0 442 137 | 8/1991 |
| EP | 0 748 615 | 12/1996 |
| WO | WO 90/07304 | 7/1990 |
| WO | WO 98/51226 | 11/1998 |
| WO | WO 2004/049961 | 6/2004 |

OTHER PUBLICATIONS

Office Action dated Nov. 16, 2009 for U.S. Appl. No. 11/600,313.
Office Action dated Jan. 21, 2010 for U.S. Appl. No. 11/140,413.

* cited by examiner

EXTENDABLE CUTTING MEMBER

PRIORITY

The application claims priority from the disclosures of U.S. Provisional Patent Application Ser. No. 60/939,355, entitled "Articulating Cavitation Device," filed May 21, 2007, U.S. Provisional Patent Application Ser. No. 60/939,365, entitled "Extendable Cutting Member," filed May 21, 2007, and U.S. Provisional Patent Application Ser. No. 60/939,362, entitled "Delivery System and Method for Inflatable Devices," filed May 21, 2007, which are herein incorporated by reference in their entirety.

BACKGROUND

Versions of the present invention relate to restoring the anatomy of fractured bone and, more particularly, to restoring the anatomy of fractured bone with an inflatable device.

Increasingly, surgeons are using minimally invasive surgical techniques for the treatment of a wide variety of medical conditions. Such techniques typically involve the insertion of a surgical device through a natural body orifice or through a relatively small incision using a tube or cannula. In contrast, conventional surgical techniques typically involve a significantly larger incision and are, therefore, sometimes referred to as open surgery. Thus, as compared with conventional techniques, minimally invasive surgical techniques offer the advantages of minimizing trauma to healthy tissue, minimizing blood loss, reducing the risk of complications such as infection, and reducing recovery time. Further, certain minimally invasive surgical techniques may be performed under local anesthesia or even, in some cases, without anesthesia, and therefore enable surgeons to treat patients who would not tolerate the general anesthesia required by conventional techniques.

Surgical procedures often require the formation of a cavity within either soft or hard tissue, including bone. Tissue cavities are formed for a wide variety of reasons, such as for the removal of diseased tissue, for harvesting tissue in connection with a biopsy or autogenous transplant, and for implant fixation. To achieve the benefits associated with minimally invasive techniques, tissue cavities are generally formed by creating only a relatively small access opening in the target tissue. An instrument or device may then be inserted through the opening and used to form a hollow cavity that is significantly larger than the access opening.

One surgical application utilizing the formation of a cavity within tissue is the surgical treatment and prevention of skeletal fractures associated with osteoporosis, which is a metabolic disease characterized by a decrease in bone mass and strength.

The disease frequently leads to skeletal fractures under light to moderate trauma and, in its advanced state, can lead to fractures under normal physiologic loading conditions. It is estimated that osteoporosis affects approximately 15-20 million people in the United States and that approximately 1.3 million new fractures each year are associated with osteoporosis, with the most common fracture sites being the hip, wrist, and vertebrae.

An emerging prophylactic treatment for osteoporosis, trauma, or the like involves replacing weakened bone with a stronger synthetic bone substitute using minimally invasive surgical procedures. The weakened bone is first surgically removed from the affected site, thereby forming a cavity. The cavity is then filled with an injectable synthetic bone substitute and allowed to harden. The synthetic bone substitute provides structural reinforcement and thus lessens the risk of fracture of the affected bone. Without the availability of minimally invasive surgical procedures the prophylactic fixation of osteoporosis-weakened bone in this manner would not be practical because of the increased morbidity, blood loss, and risk of complications associated with conventional procedures. Moreover, minimally invasive techniques tend to preserve more of the remaining structural integrity of the bone because they minimize surgical trauma to healthy tissue.

Other less common conditions in which structural reinforcement of bone may be appropriate include bone cancer and avascular necrosis. Surgical treatment for each of these conditions can involve removal of the diseased tissue by creating a tissue cavity and filling the cavity with a stronger synthetic bone substitute to provide structural reinforcement to the affected bone.

Medical balloons are commonly known for dilating and unblocking arteries that feed the heart (percutaneous translumenal coronary angioplasty) and for arteries other than the coronary arteries (noncoronary percutaneous translumenal angioplasty). In angioplasty, the balloon is tightly wrapped around a catheter shaft to minimize its profile, and is inserted through the skin and into the narrowed section of the artery. The balloon is inflated, typically, by saline or a radiopaque solution, which is forced into the balloon through a syringe. Conversely, for retraction, a vacuum is pulled through the balloon to collapse it.

Medical balloons also have been used for the treatment of bone fractures. One such device is disclosed in U.S. Pat. No. 5,423,850 to Berger, which teaches a method and an assembly for setting a fractured tubular bone using a balloon catheter. The balloon is inserted far away from the fracture site through an incision in the bone, and guide wires are used to transport the uninflated balloon through the medullary canal and past the fracture site for deployment. The inflated balloon is held securely in place by the positive pressure applied to the intramedullary walls of the bone. Once the balloon is deployed, the attached catheter tube is tensioned with a calibrated force measuring device. The tightening of the catheter with the fixed balloon in place aligns the fracture and compresses the proximal and distal portions of the fractured bone together. The tensioned catheter is then secured to the bone at the insertion site with a screw or similar fixating device.

BRIEF DESCRIPTION OF THE FIGURES

It is believed that versions of the present invention will be better understood from the following description taken in conjunction with the accompanying drawings. The drawings and detailed description that follow are intended to be merely illustrative and are not intended to limit the scope of the invention.

DETAILED DESCRIPTION OF THE INVENTION

Figure 1:
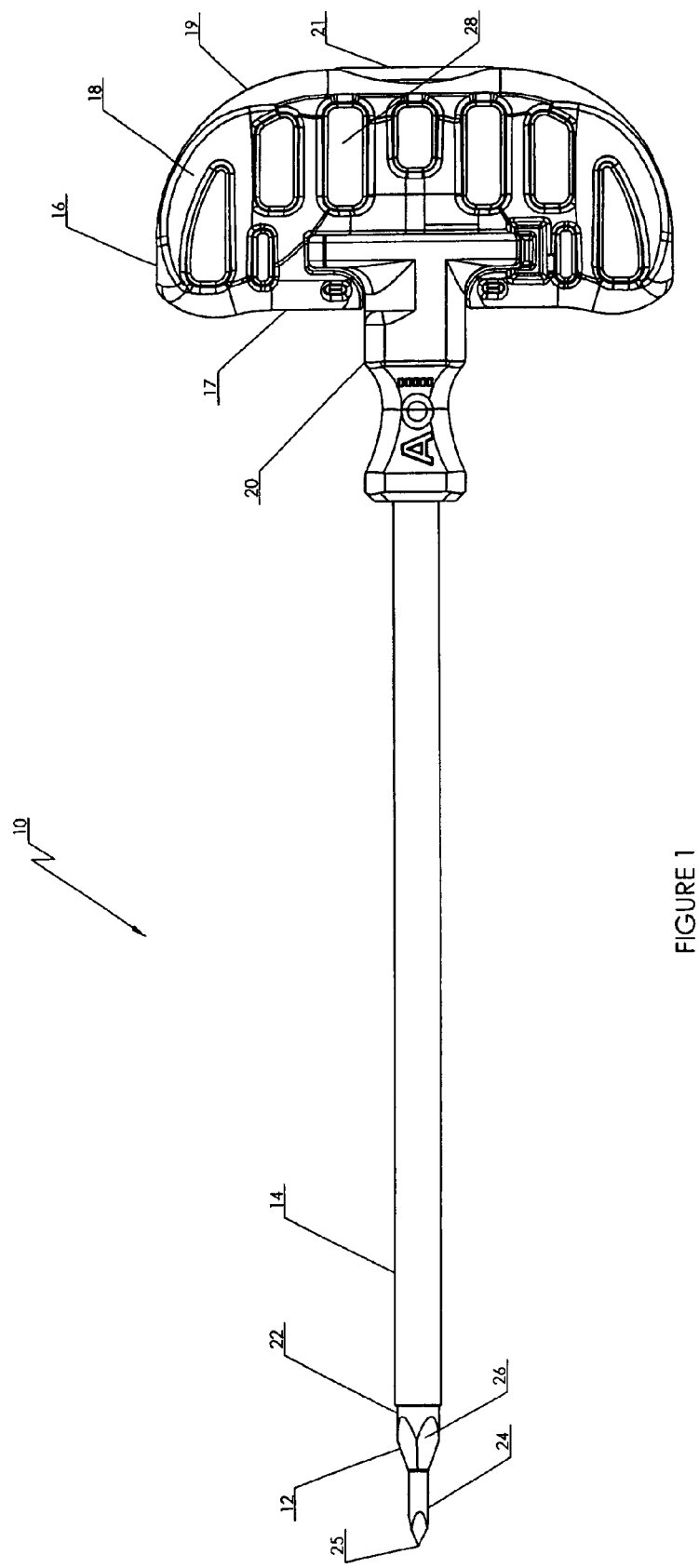
FIG. 1 depicts a perspective side view of one version of a trocar and cannula assembly of a vertebral cavity formation and fracture reduction system.

Referring to FIG. 1, disclosed is one version of a trocar and cannula assembly (10) of a vertebral cavity formation and fracture reduction system and method used to access a vertebral body. The assembly (10) includes a trocar (12) and a cannula (14) associated with a composite or two-part handle (16). The two-part handle (16) is configured for rotation and includes a first detachable handle portion (18) coupled to the trocar (12) and a second handle portion (20) coupled to the cannula (14). Rotation of the handle (16) and/or trocar and cannula assembly (10) may be accomplished in any suitable manner such as with manual rotation or with a motor. The handle (16) is shown as being symmetrical; however, any suitable offset or asymmetrical shape is contemplated. The two-part handle (16) has a distal surface (17) that is gripped by a user's fingers and a proximal surface (19) that is gripped by the user's palm. The distal surface (19) of the two-part handle (16) may have any suitable surface effect such as, for example, defined finger grips, a curved surface, a generally flat surface, concavities, and/or convexities. The proximal surface (19) on the first detachable handle portion (18) may include a surface (21) configured to accept a hammer strike.

The distal tip (25) of the trocar (12) is configured to access and penetrate the cortical bone of a vertebra, where the vertebra is accessed with the trocar and cannula assembly (10) engaged. Once the vertebra has been accessed by the distal tip (25) of the trocar (12), the cannula (14) may be urged into the passage formed by the trocar (12). The trocar (12), which may be configured from stainless steel, is removable from the cannula (14) after accessing the vertebra Removal of the trocar (12) from the assembly (10) leaves the cannula (14) in place, for example, within the cortical wall of the vertebra as an instrument conduit for the insertion of any suitable instrument or device. In the illustrated version, the trocar (12) is withdrawn from the cannula (14) by removing the first detachable handle portion (18) from the assembly (10) until the trocar (12) is pulled proximally from the cannula (14). The trocar (12) and cannula (14) are shown in more detail in FIGS. 2 and 3.

Figure 2:
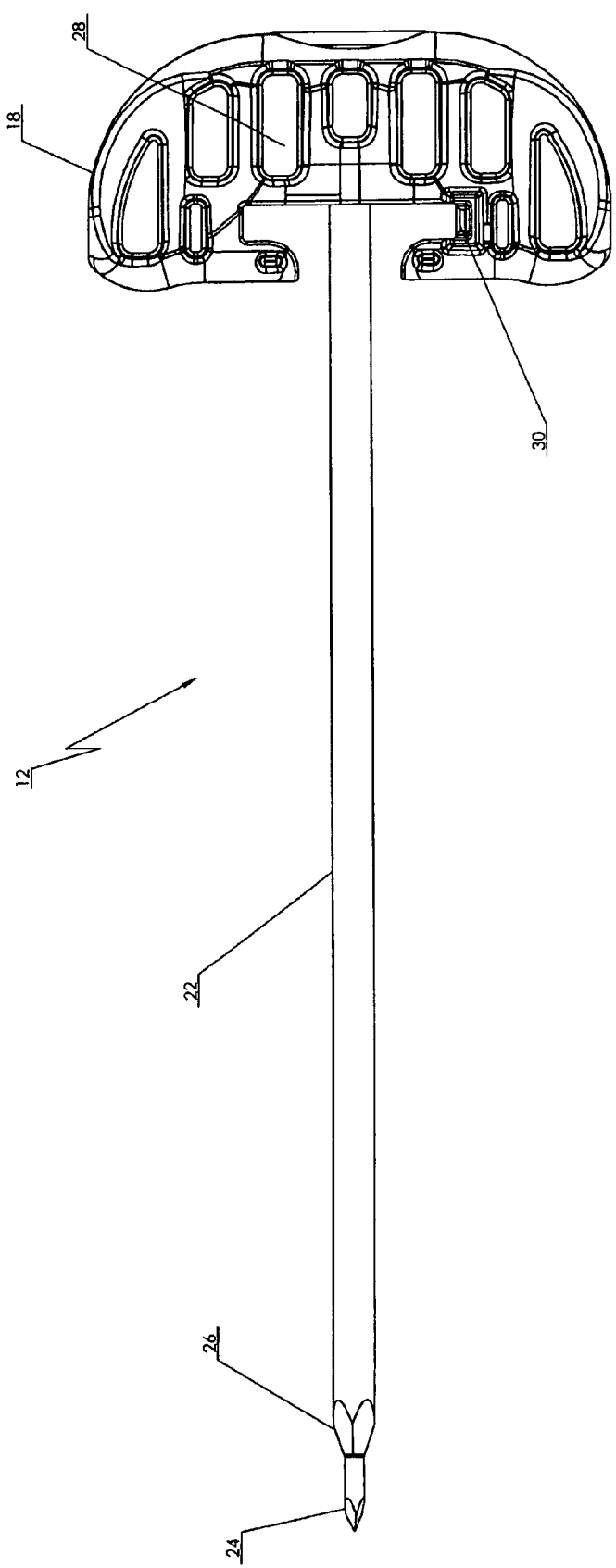
FIG. 2 depicts a perspective side view of the trocar of FIG. 1 shown after removal from the cannula of the assembly.

Referring to FIG. 2, one version of the trocar (12) is shown after removal from the cannula (14) of the assembly (10). The trocar (12) includes an elongate cylindrical body (22) having a proximal end and a distal end, where the proximal end of the body (22) is coupled with the first detachable handle portion (18) and the distal end includes the distal tip (25), shown in FIG. 1, a first penetration member (24), and a second penetration member (26). In the illustrated version, the first detachable handle portion (18) includes a grip (28) to facilitate rotation of the penetration members (24) and (26) to access the vertebra and create a passage into the vertebra. The grip (28) may also be used to facilitate decoupling the handle portion (18) from the two-part handle (16). The handle portion (18) further includes a coupling (30) configured to detachably engage the second handle portion (20) associated with the cannula (14). Uncoupling the handle portion (18) from the handle portion (20) allows the trocar (12) to be removed from the cannula (14).

The first penetration member (24) of the trocar (12) is a cylindrical body having a plurality of intersecting flats, bevels, or faces that form a point at the distal tip (25) configured to penetrate tissue and vertebral bone with manual rotation and longitudinal articulation. The first penetration member (24) is configured to provide the initial access, after an incision is made, through a patient's skin and into the cortical bone of a vertebra. The relatively small diameter of the first penetration member (24) facilitates insertion and positioning or repositioning of the trocar (12). The second penetration member (26) is a transition between the smaller diameter first penetration member (24) and the larger diameter body (22) of the trocar (12) and includes a plurality of flats configured to expand the diameter of the passage. In one version, the wider second penetration member (26) has sharp edges that facilitate cutting of bone. Providing dual diameter or stepped tips may ease insertion and improve the stability of the trocar (12). The stepped penetration members (24) and (26) increase the size of the access point to a diameter sufficient to accept the cannula (14) for insertion and retention within the vertebra.

It will be appreciated that the trocar (12) may be configured with any suitable features to facilitate vertebral access, skiving, penetration of cortical bone, or any other suitable use. The trocar (12) may include one or a plurality of stepped tips, including the first and second penetration members (24) and (26), having any suitable cutting effects, diameters, shapes, and/or configurations. The one or a plurality of penetration members may be sharp, dull, fluted, or have any other suitable configuration. The distal end of the trocar (12) may be tapered, have movable cutting members, or may be coated or otherwise associated with materials, such as diamond, that facilitate cutting.

Figure 3:
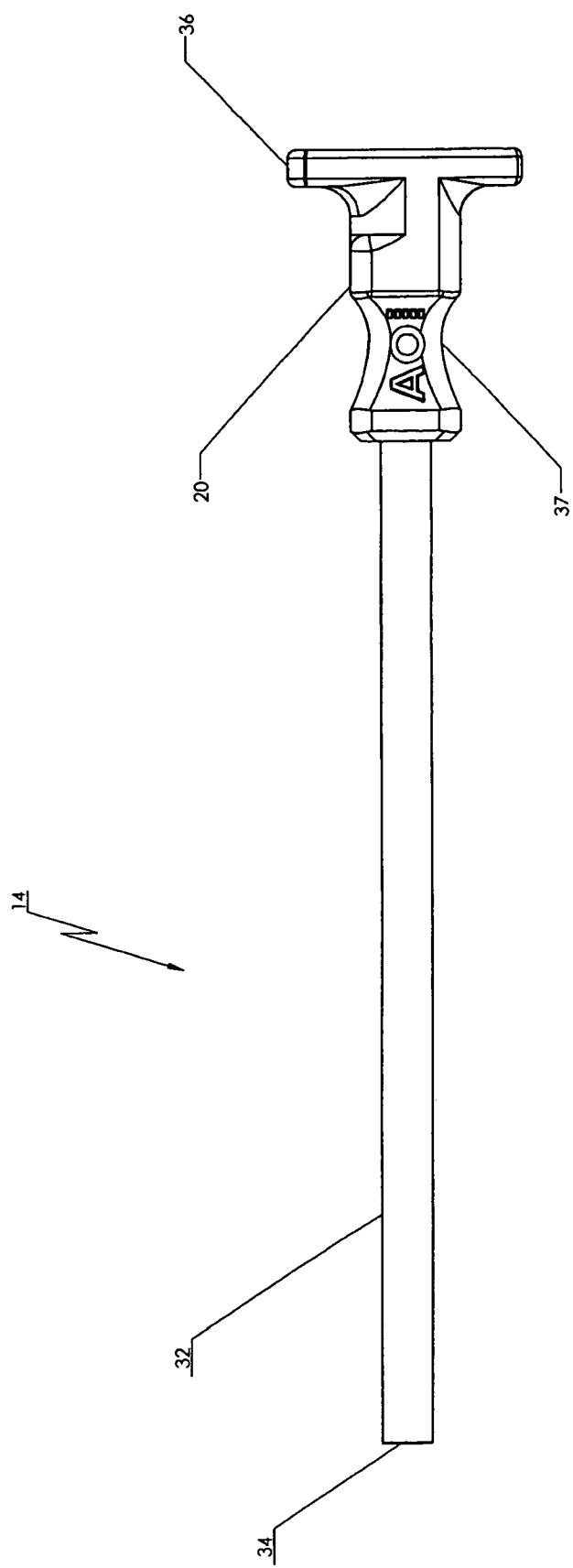
FIG. 3 depicts a perspective side view of the cannula of FIG. 1 shown after removal of the trocar from the assembly.

Referring to FIG. 3, the cannula (14) is shown after removal of the trocar (12) from the assembly (10) shown in FIG. 1. Generally, the cannula (14) is configured to function as an instrument conduit to the intervertebral space, or any other suitable tissue space, after the initial access point has been formed and the trocar (12) removed. The cannula (14) may be retained within the vertebral cortical bone for the duration of the procedure while the second handle portion (20) remains outside the patient's body as an access port. The cannula (14) includes an elongate cylindrical body (32) defining a lumen having a proximal end and a distal end, where the proximal end of the body (32) is coupled with the second handle portion (20) and the distal end includes an aperture (34) through which the trocar (12) and other instruments are configured to pass. The second handle portion (20) includes a coupling (36) configured to engage the coupling (30) of the first detachable handle portion (18), shown in FIG. 2, in a rotating snap fit. The second handle portion (20) includes a bore similarly sized and coaxial with the lumen of the cylindrical body (32) to accept instrumentation. The cannula (14) further includes a grip (37) that facilitates positioning and removal of the cannula (14) once the trocar (12) is removed. The grip (37) may be separate and distinct from the distal surface (17) of the two-part handle or, alternatively, when the two-part handle (16) is coupled in the assembly (10) the grip (37) and distal surface (17) may form a contiguous or substantially contiguous surface. In this manner, the grip (37) and the distal surface (17) may both be used for rotation of the handle (16) to facilitate vertebral access. Providing a two-part handle having a contiguous grip (37) and distal surface (17) may facilitate use of the assembly (10), shown in FIG. 10, while providing effective gripping surfaces for use of the cannula (14) and trocar (12) separately.

Figure 4:
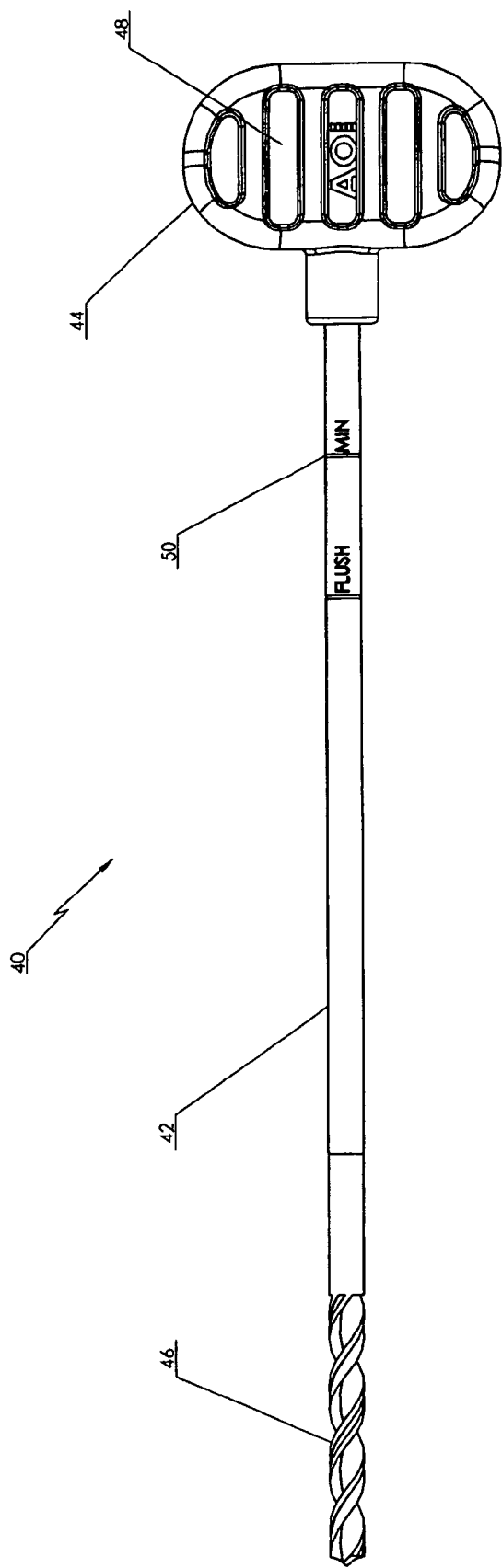
FIG. 4 depicts a perspective side view of one version of a drill that is configured for insertion through the cannula of FIG. 3.

Referring to FIG. 4, one version of a drill (40) is shown that is used in accordance with a vertebral cavity formation and fracture reduction system and method. The drill (40) includes an elongated, stainless steel cylindrical body (42) having a distal end and a proximal end, where the proximal end is coupled to a handle (44) and the distal end is configured as a drill bit (46). The body (42) of the drill (40) is sized to fit through the central lumen of the cannula (14) and, after introduction into the cannula (14), the drill bit (46) is used to form, for example, an access passage in the cancellous bone of the vertebra. The handle (44) is provided with a grip (48) to facilitate manual rotation of the drill (40) within the cancellous bone of the vertebra to form a passage up to the anterior cortex. The body (42) is provided with markings (50) to indicate the minimum depth required for the insertion of subsequent instruments. Following creation of the access passage, the drill (40) is configured for removal through the cannula (14). Any suitable markings (50) may be provided using any suitable metric to determine proper insertion.

Figure 5:
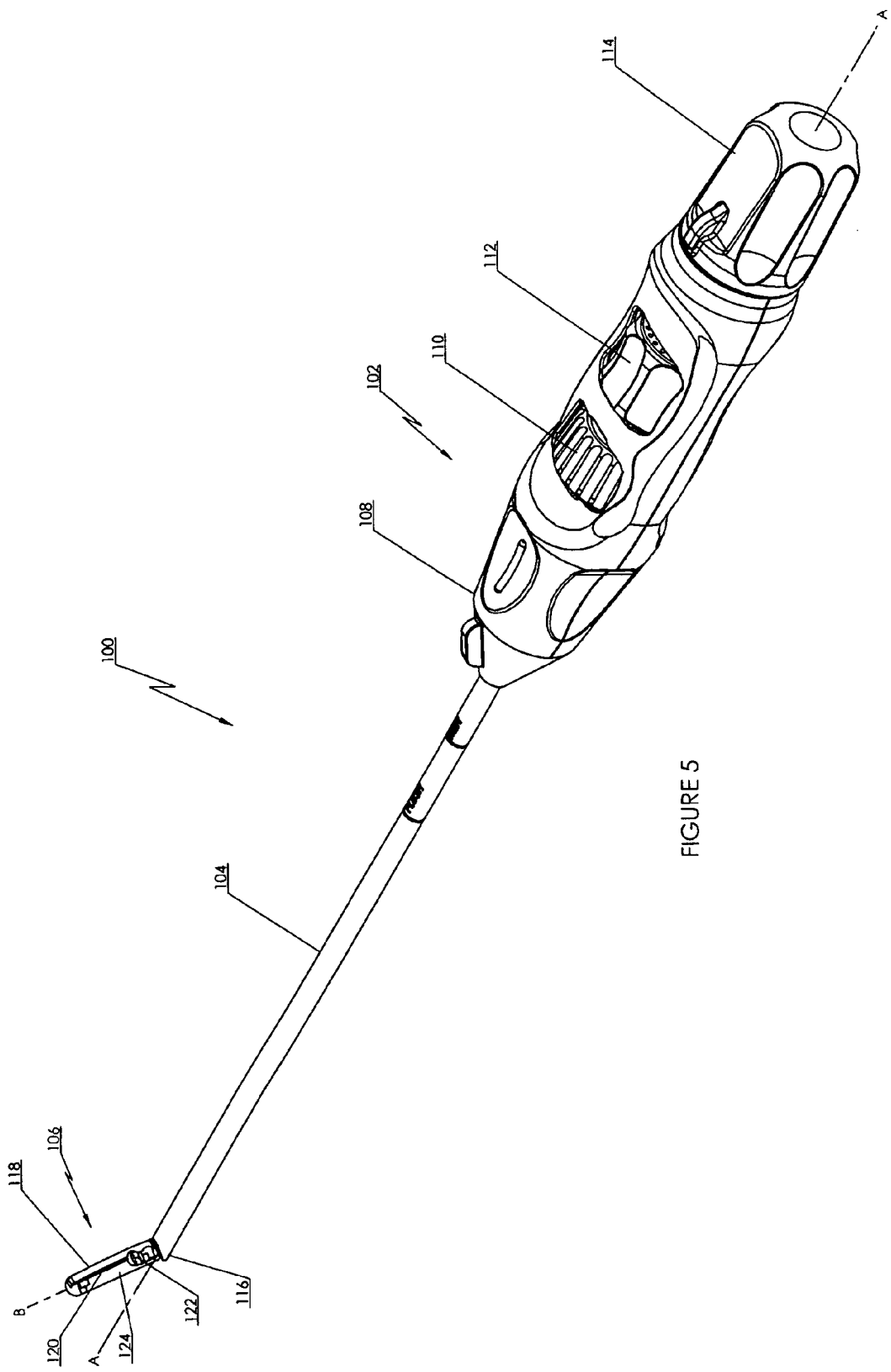
FIG. 5 depicts a perspective view of one version of a cavity formation instrument of a vertebral cavity formation and fracture reduction system shown in the articulated position.

Referring to FIG. 5, disclosed is one version of an articulating cavity formation instrument (100) that may be used to form a tissue cavity in, for example, cancellous bone within a vertebral body. In one version, the cavity formation instrument (100) is approximately 40 cm in length and includes, generally, a handle (102), an insertion member, such as insertion tube (104), and an end effector (106) configured for articulation. The handle (102) has a generally cylindrical body, having a proximal end and a distal end, aligned along a first linear axis A-A. The handle (102) includes a body (108) and a series of rotational actuation members (110), (112), and (114), that are rotatable about the first linear axis A-A to articulate various aspects of the end effector (106). In the illustrated version, the rotational members (110) and (112) are knobs secured to the center shaft (128), shown in FIG. 6, and are retained within the body (108) of the handle (102). Rotational member (114) is secured to the body (108) of handle (102) by a mating flange. It will be appreciated that the illustrated rotational actuation members (110, (112), and (114) are described by way of example only, where any suitable mechanism, such as slides, levers, geared components, or the like, including combinations thereof, may be used to actuate the cavity formation instrument (100).

The insertion tube (104) of the vertebral cavity formation and fracture reduction system extends axially along the first linear axis A-A from the distal end of the handle (102) to the proximal end of the end effector (106). The insertion tube (104) may be stainless steel and defines an interior lumen having an opening at both ends. In the illustrated version, with particular reference to FIG. 8, a pivot pin (116) is welded to the insertion tube (104), where the pivot pin (116) is transverse to and offset from the first linear axis A-A. As will be described herein, the pivot pin (116) facilitates articulation of the end effector (106) such that it is offset from the first linear axis A-A. The pivot pin (116) is one example of an articulation region of the instrument (100)

The end effector (106), which has a proximal portion (122) and a distal portion (124), is located at the distal end of the insertion tube (104) and is configured to rotate and articulate relative to the insertion tube (104). The proximal portion (122) of the end effector (106) is coupled to the insertion tube (104) with the pivot pin (116) such that the end effector (106) is restrained from axial movement relative to the insertion tube (104), but is rotatable about the pivot pin (116). In this manner, the end effector (106) can be articulated such that it is offset from first linear axis A-A into alignment, for example, with the second linear axis B-B. The second linear axis B-B is described by way of example only, where any suitable degree or distance of articulation is contemplated.

The distal portion (124) of the end effector (106) which may be, for example, from 1.8 cm to 2.8 cm in length, is configured to rotate, relative to the proximal portion (122) of the end effector (106), about the central axis A-A of the end effector (106). The distal portion (124) of the end effector may also be rotated about the second linear axis B-B, or any other suitable offset axis, when the end effector (106) is in an articulated position. Rotation of the end effector (106), in both the articulated and unarticulated position, facilitates cavity formation by allowing cancellous bone to be cut about or around multiple axes. Providing a wide range of axes about which portions of a cavity can be formed facilitates the creation of a wide range of cavity configurations that may provide greater therapeutic effect.

The end effector (106) further includes a lateral aperture (120) and an aperture (134) through which a deformable cutter (118) is extended and retracted. In the illustrated version, the deformable cutter (118) is an elongate, stainless steel flexible band that may be between 1.5 cm to 3 cm in length; however, any suitable cutting element such as, for example, a wire, an energized cutting element, a filament, a cutting element having a free end, a cutting element having memory retention properties, and/or a cutting element that expands outwardly with rotation may be utilized. Any suitable shape such as oval, triangular, or elliptical is contemplated. In the illustrated version, the distal end of the cutter (118) is fixedly coupled to the end effector (106) and the proximal end of the cutter is attached via a junction member (132) to a movable shaft (128) configured to rotate and translate within the insertion tube (14). The cutter (118) is threaded through the aperture (134) in the distal end of the end effector (106) and is fixedly coupled to a more proximal portion of the end effector, as illustrated in FIG. 8, to form an expandable and retractable cutter.

Figure 6:
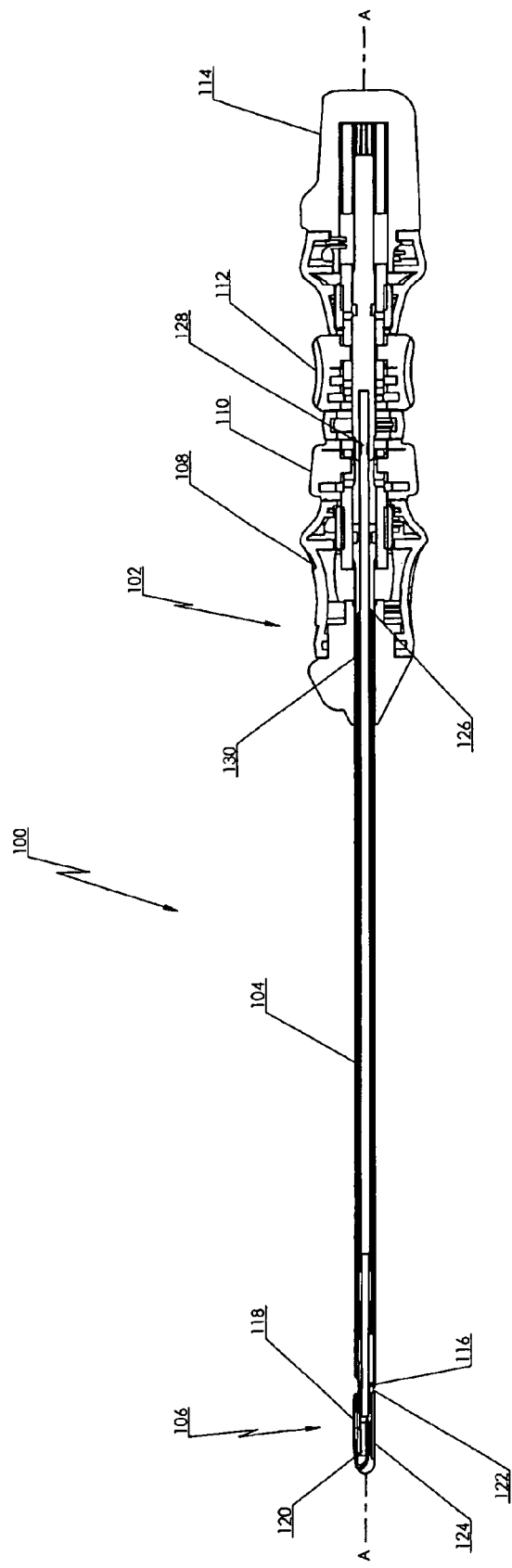
FIG. 6 depicts a longitudinal, cross-section view of the cavity formation instrument of FIG. 5 shown in the unarticulated position.
Figure 7:
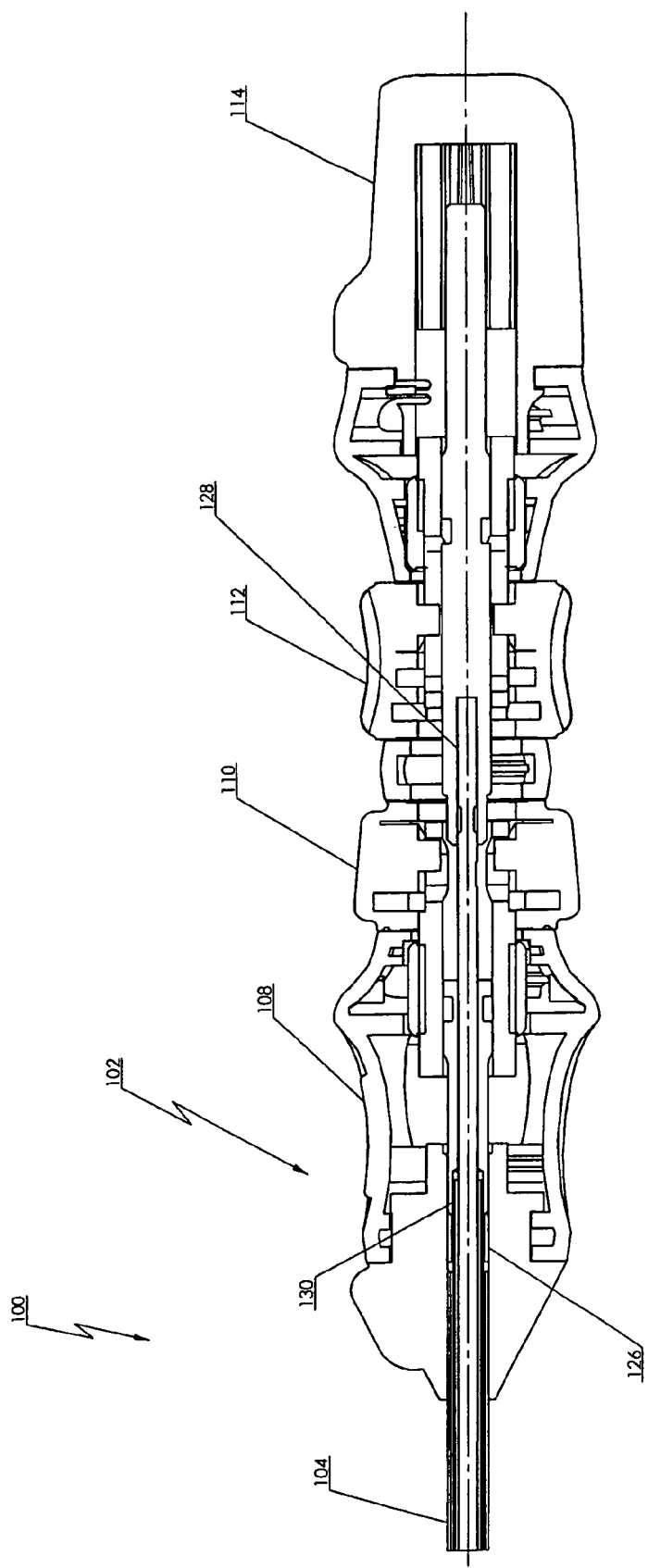
FIG. 7 depicts a more detailed view of the longitudinal, cross-section view of FIG. 6 showing the handle portion of the cavity formation instrument.
Figure 8:
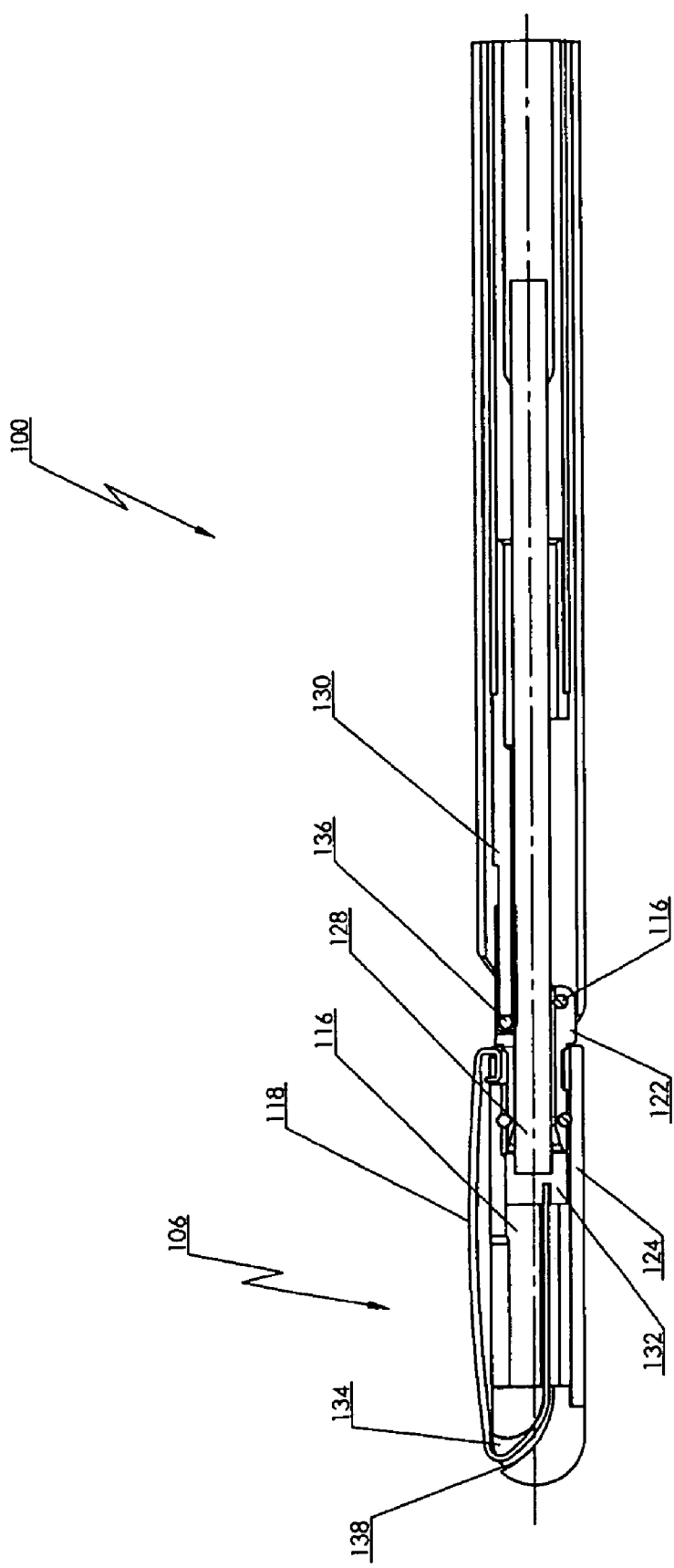
FIG. 8 depicts a more detailed view of the longitudinal, cross-section view of FIG. 6 showing the end effector potion of the cavity formation instrument in the unarticulated position.

FIGS. 6-8 illustrate longitudinal, cross-section views of the cavity formation instrument (100) of the vertebral cavity formation and fracture reduction system and method. FIG. 7 illustrates a more detailed view of the handle (102) and FIG. 8 illustrates a more detailed view of the end effector (106). Referring to FIGS. 6 and 7, a central channel (126) is depicted that extends along the first linear axis A-A within the body (108) of the handle (102). The proximal end of the insertion tube (114) is affixed within this channel (126) such that the insertion tube (104) and the channel (126) are coaxial. A shaft (128) is provided that extends from a coupling with the rotational member (114) through the interior lumen of the insertion tube (104) to a coupling at the junction member (132) associated with the distal portion (124) of the end effector (106).

Referring to FIG. 7, the shaft (128) is associated with the rotational member (114) such that rotation of the rotational member (114) correspondingly rotates the shaft (128) and the attached distal portion (124) of the end effector (106). Thus, the rotational member (114) is used to rotate the end effector (106) and cutter (118) relative to the insertion tube (104). In the illustrated version, the rotational member (114) and the shaft (128) are not coupled for axial translation, only rotational translation, where axial translation of the shaft (128) is independent from the operation of the rotational member (114). The rotational member (114) is used to rotate the end effector (106) when the cutter (118) is extended to rotationally cut tissue to form a tissue cavity, for example, wholly within a vertebra.

Referring to FIG. 7, the center rotational member (112) is associated with the shaft (128) to facilitate expansion and retraction of the cutter (118) through the aperture (134). The rotational member (112) is threadedly engaged with the shaft (128) in a jack screw configuration such that rotational movement of the rotational member (112) is translated as axial movement to the shaft (128). The shaft (128) is freely rotatable relative to the rotational member (112) such that only axial motion, and not rotational articulation, is translated to the shaft (128) by the rotational member (112). As discussed previously, rotation of the shaft (128) may be controlled independently by the proximal rotational member (114). The rotation and axial translation of the shaft (128), in the illustrated version, are distinct and separate operations with independent mechanisms to give the cavity formation instrument (100) operational flexibility.

Referring to FIG. 8, axial translation of the shaft (128) causes the junction member (132) to urge the proximal end of the cutter (118) in a corresponding proximal or distal direction. Translating the shaft (128) in the distal direction, such as by rotating the rotational member (112) in a first direction, urges the cutter (118) against an abutment (138) and outwardly through the aperture (134), thus expanding the cutter outwardly to increase the cutting radius. Translating the shaft (128) in the proximal direction, such as by rotating the rotational member (112) in a second direction, urges the cutter (118) to retract through the aperture (134) and against a transverse member, thus reducing the cutting radius. The rotational member (112), shown in FIG. 7, can be used to adjust the cutting radius of the cavity formation instrument (100) to a desired radius prior to rotating the cutter (118) to form a cavity. In an alternate version, the cutter (118) can be extended or retracted simultaneously while rotating the end effector (106) to form a cavity.

Figure 9:
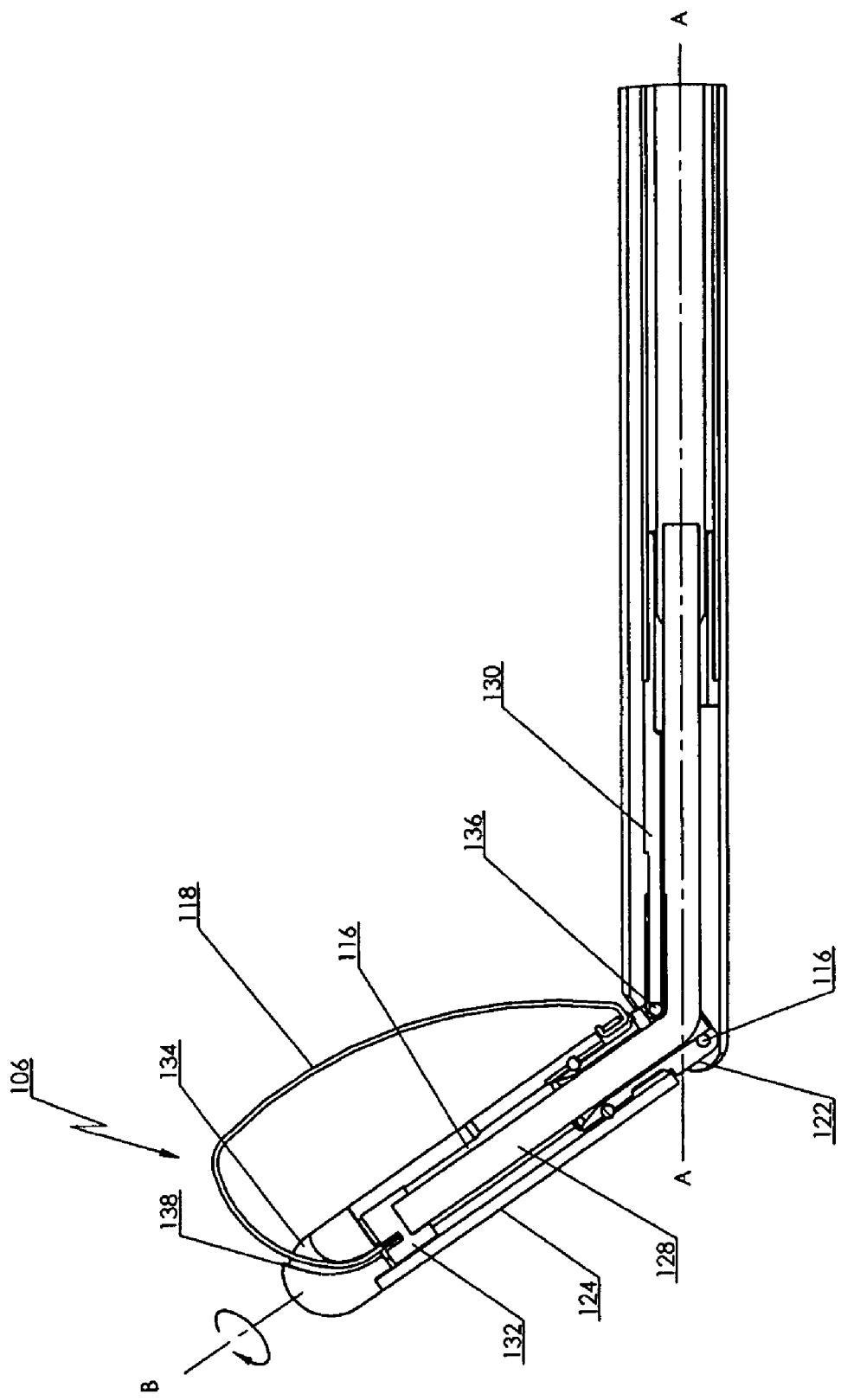
FIG. 9 depicts a more detailed view of the longitudinal, cross-section view of FIG. 6 showing the end effector potion of the cavity formation instrument in the articulated position.

Referring to FIG. 7, the distal rotational member (110) is associated with an articulation drive member (130) to facilitate articulation of the end effector from the first linear axis A-A to the second linear axis B-B, shown in FIG. 9. The rotational member (110) is threadedly engaged with the drive member (130) in a jack screw configuration such that rotational movement of the rotational member (110) is translated as axial movement to the drive member (130). The distal end of the drive member (130) is coupled to proximal portion (122), shown in FIG. 8, of the end effector (106) with a pin (136). Drawing the drive member (130) and pin (136) proximally causes the end effector (106) to rotate about the pivot pin (116). Articulating the end effector (106) in such a manner allows the end effector to be positioned along a second linear axis B-B, shown in FIG. 9, offset from the first linear axis A-A. When in the offset position, the cutter (118) may be extended with the rotational member (112) and rotated with the rotational member (114) to increase the volume of a cavity. The end-effector (106) is realigned with the first linear axis B-B by urging the drive member (130) and pin (136) distally.

FIG. 9 illustrates a longitudinal, cross-sectional view of the end effector (106) shown in the articulated position with the cutter (118) extended. The end effector (106) has been articulated into alignment with the second linear axis B-B by axially translating the drive member (130) and rotating the end effector (106) about the pivot pin (116). Articulation of the end effector (106) may occur at any suitable articulation region or point such as, for example, the pivot pin (116), a geared articulation region, a hinge, a metal hinge, a plastic material, a flexible member, a living hinge in flexible material, a shape memory alloy articulation region, or combinations thereof One or a plurality of articulation regions or points, such as pivot pins (116), may be provided to allow for articulation about multiple planes and/or axes. Articulation may be mechanical, such as with a pivot pin or a geared configured, in a manner that excludes flexible or living hinge components at the articulation point or region. As described in the illustrated version, the drive member (130) is proximally and distally translated by rotating the rotational member (110). The cutter (118) is shown in the extended position after the shaft (128) has been urged distally by rotating the rotational member (112). In the position shown in FIG. 9, the distal portion (124) of the end effector (106) is rotated to form a cavity portion about the second linear axis B-B.

Articulation of the end effector (106) allows for an offset cavity portion to be formed while the insertion tube (104) remains aligned with the first linear axis A-A. The offset cavity portion of the intervertebral cavity facilitates central placement of the balloon (212), which may be advantageous under certain circumstances. For example, an offset cavity may be useful depending on the geometry of the bone, in creating an anchor to provide more torque in an asymmetrical cavity, creating an undercut, or for accessing regions of a bone offset from the access point. Creating an offset cavity may allow for larger cavities to be created. Generally, the range of cavities and access may be increased while permitting the instrument to be inserted through a relatively small access point.

Figure 10:
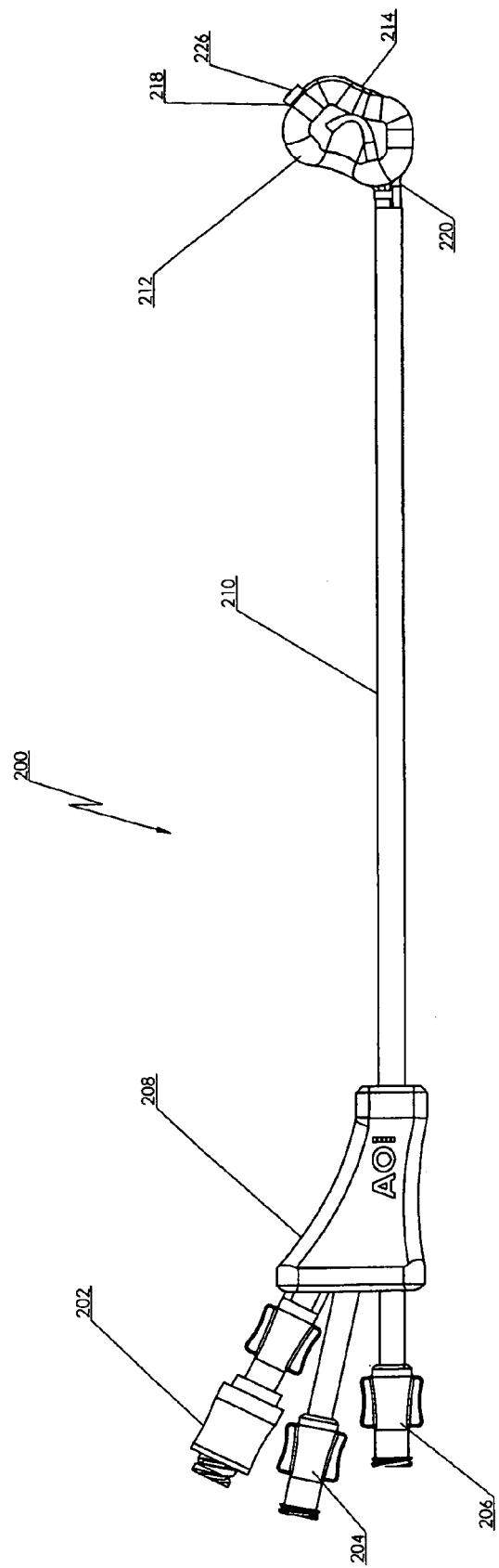
FIG. 10 depicts a perspective side view of one version of a vertebral fracture reduction apparatus of a vertebral cavity formation and fracture reduction system.

Referring to FIG. 10, disclosed is one version of a vertebral fracture reduction apparatus (200) of the vertebral cavity formation and fracture reduction system. The vertebral fracture reduction apparatus (200) is approximately 32 cm in length and includes, generally, a series of flexible access ports (202), (204), and (206), a port housing (208), an insertion sheath (210), a central dual lumen (218), a side lumen (220), an inflatable member or balloon (212), and a delivery tentacle (214). The apparatus (200) is configured for insertion into a cut vertebral cavity in a deflated configuration and for expansion within the cavity to reduce a vertebral compression fracture. Once the fracture is reduced, the apparatus (200) is configured to deliver bone cement into the vertebral cavity to restore the integrity of the vertebra. Any suitable dimension may be provided where, for example, the apparatus (200) may be any length sufficient to reach a target site without interfering with a fluoroscope.

Figure 11:
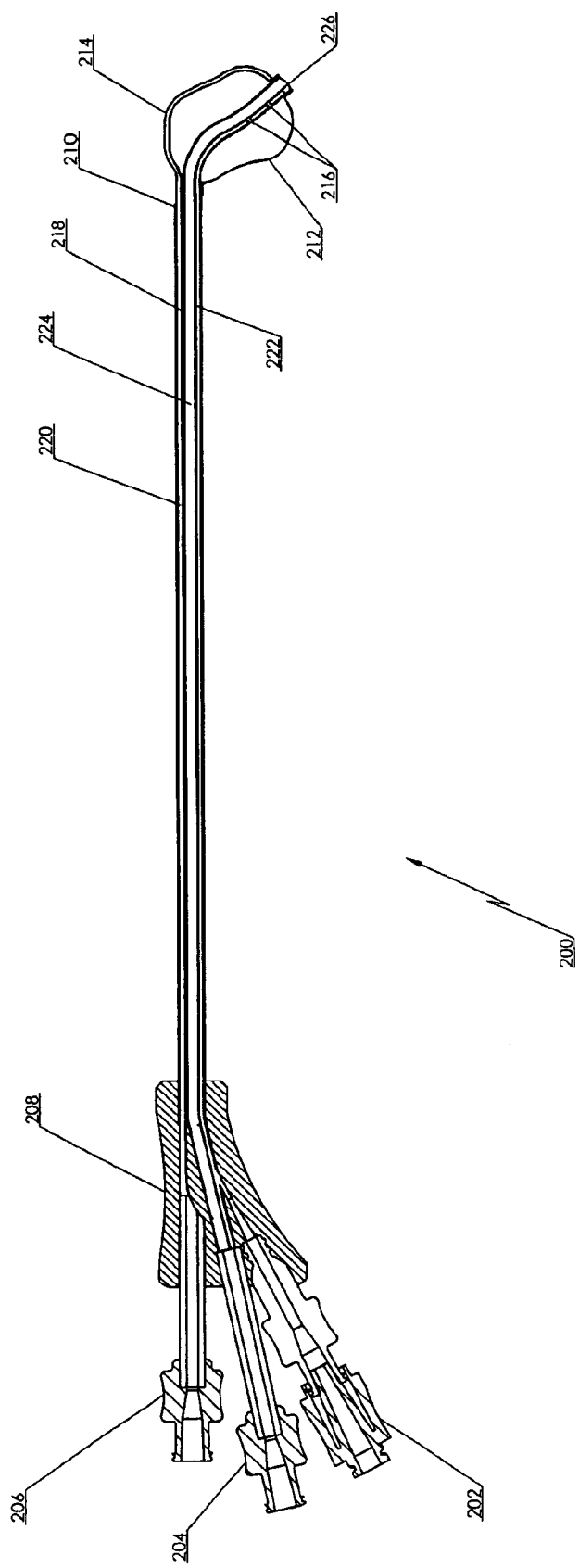
FIG. 11 depicts a longitudinal, cross-section view of the vertebral fracture reduction apparatus of FIG. 10.
Figure 12:
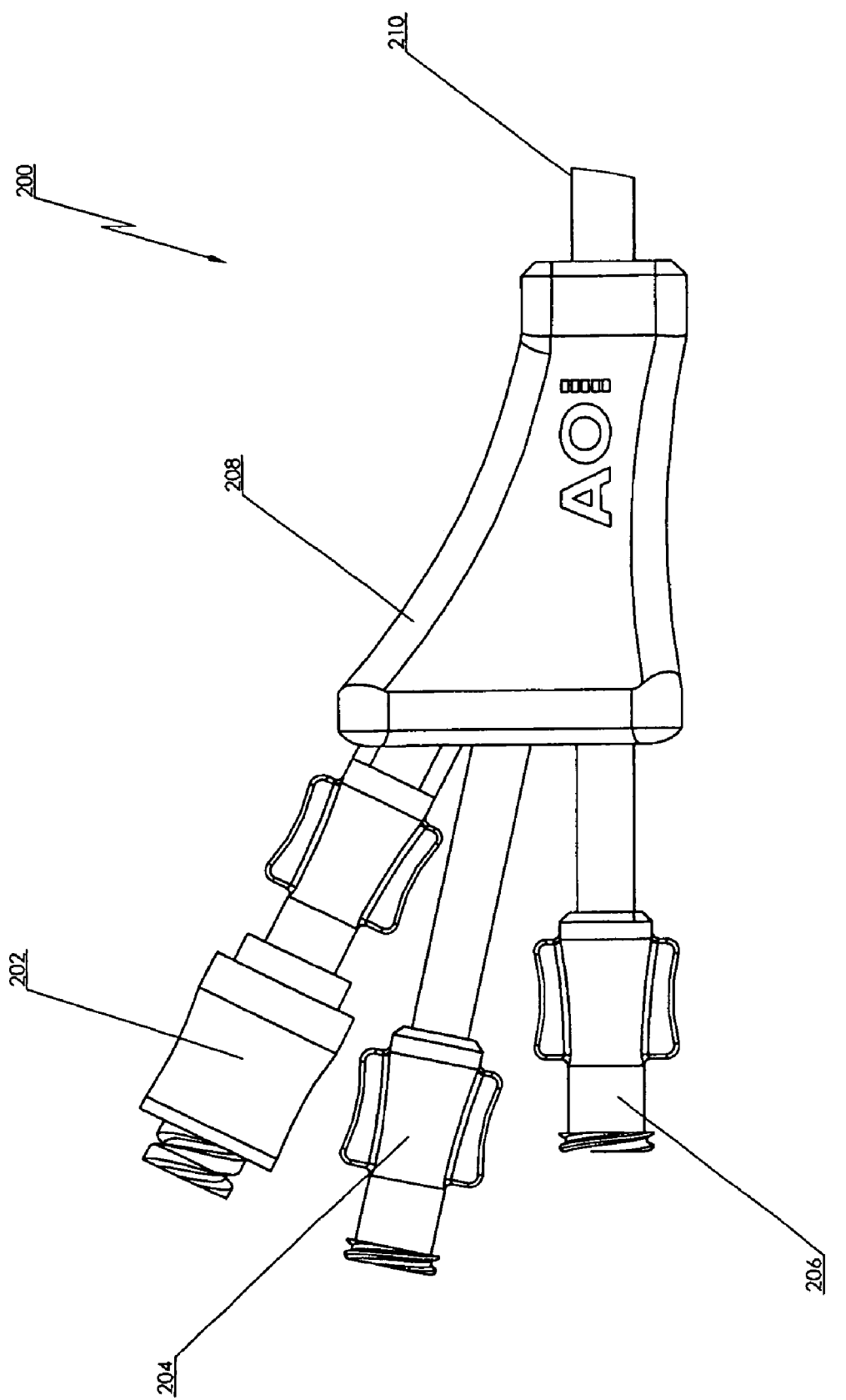
FIG. 12 depicts a more detailed perspective side view of the access ports and port housing of the vertebral fracture reduction apparatus of FIG. 10.
Figure 13:
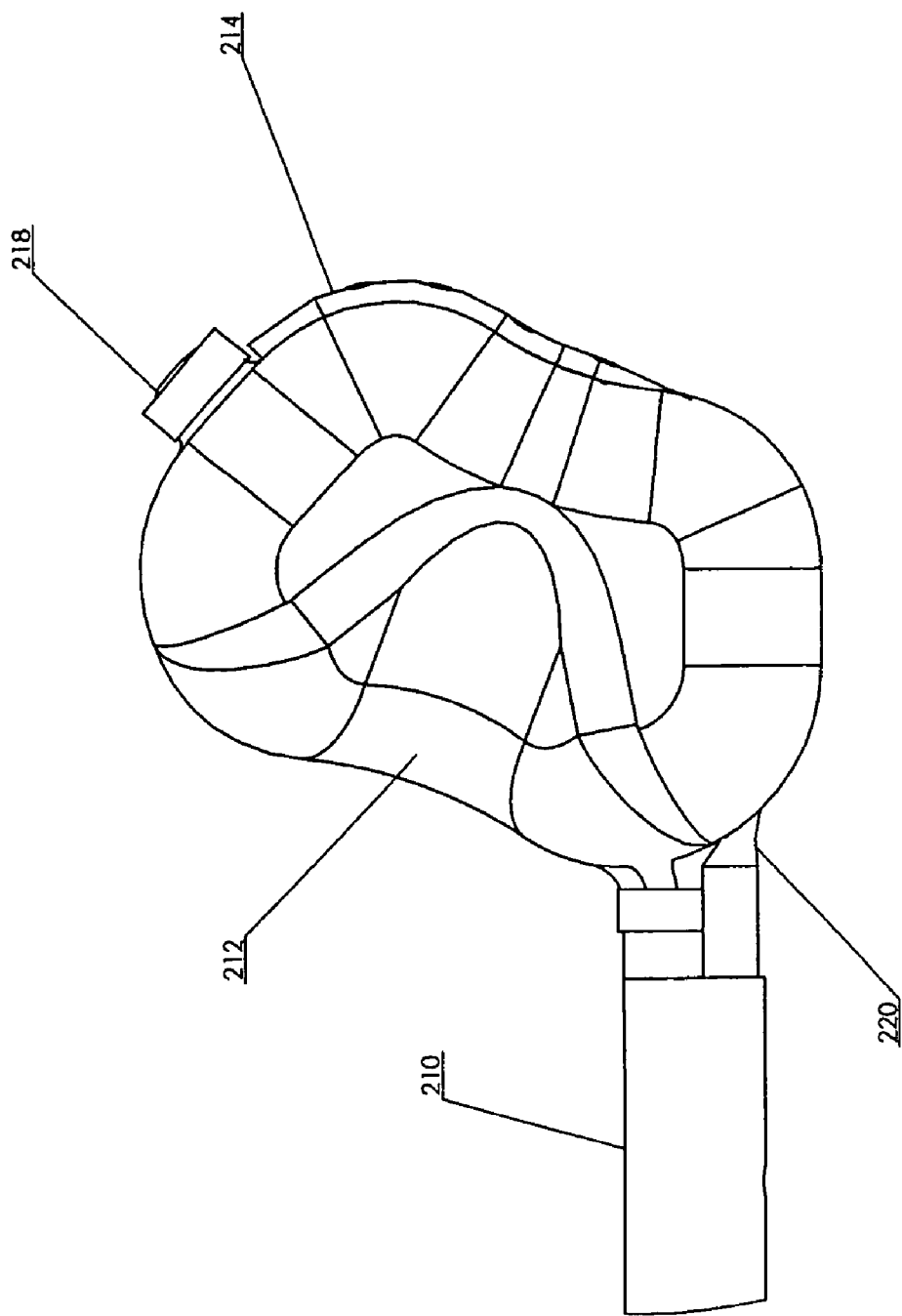
FIG. 13 depicts a more detailed perspective side view of the balloon and delivery tentacle of the vertebral fracture reduction apparatus of FIG. 10.
Figure 14:
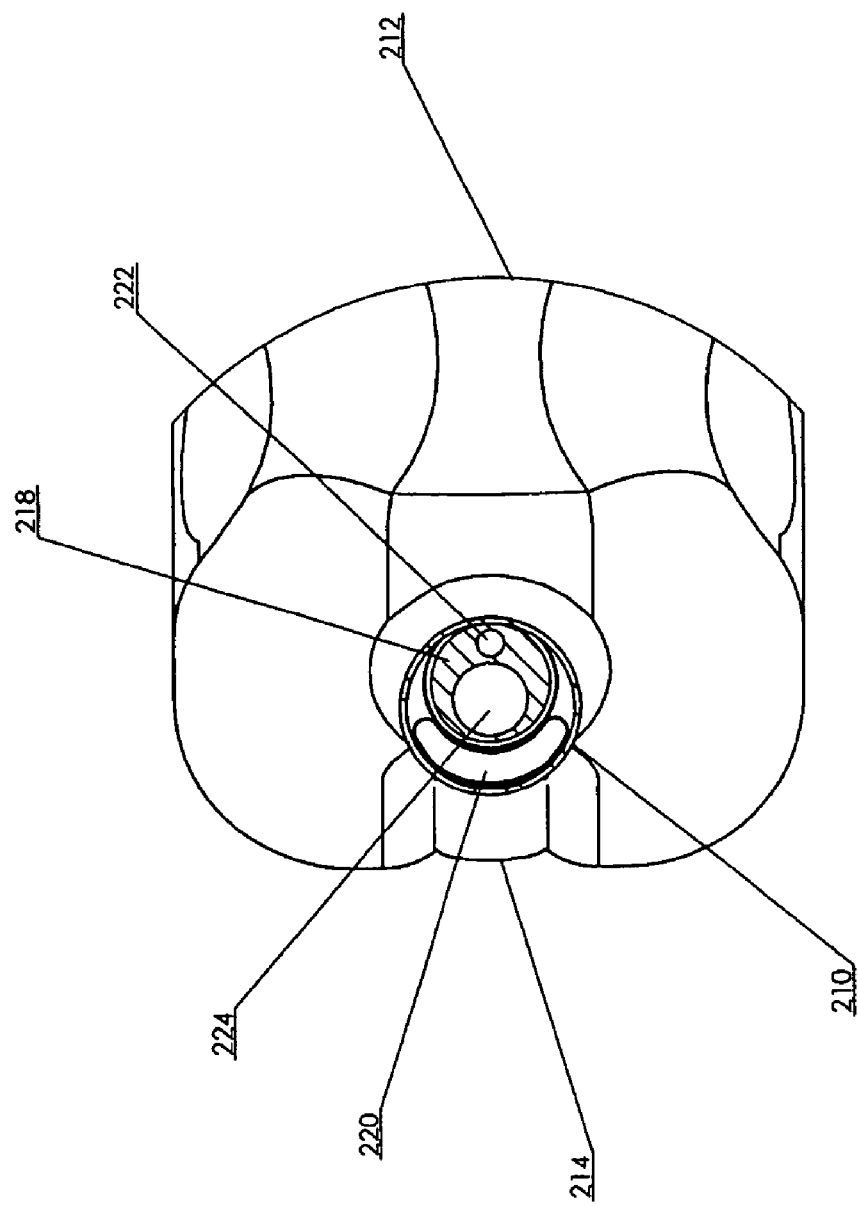
FIG. 14 depicts a transverse, cross-section view of the balloon, delivery lumens, and insertion sheath of the vertebral fracture reduction apparatus of FIG. 10.

FIG. 11 illustrates a longitudinal, cross-sectional view of the vertebral fracture reduction apparatus (200) of the vertebral cavity formation and fracture reduction system. FIG. 12 illustrates a more detailed view of the handle access ports (202), (204), (206), and port housing (208). FIG. 13 illustrates a more detailed view of the balloon (212) and delivery tentacle (214). FIG. 14 is a cross-sectional view of the delivery lumen and insertion sheath. Referring to FIGS. 11 and 12, the aligned access ports (202), (204), and (206) have a coplanar orientation and each include a luer connection configured to engage a single-plunger delivery syringe. Access ports (202) and (204) are associated with the central dual lumen (218) and the access port (206) is associated with the side lumen (220). Any suitable type or number of ports may be provided where, for example, the ports may be configured to prevent accidental use of an incorrect syringe or applicator with color coding, varying dimensions, varying connections, or the like. Any suitable delivery apparatus may be used including syringes, screw-type plungers, push plungers, pistol plungers, pressurized devices, motorized pumps, or the like.

Referring to FIGS. 10 and 11, in the illustrated version the central dual lumen (218) is an elongated, semi-rigid cylindrical body that is extruded with bismuth, a radiopaque additive, to facilitate visualization during surgery. The dual lumen (218) is associated with access ports (202) and (204) and extends from the housing (208) through the balloon (212) and distally from the end of the balloon. The dual lumen (218) passing through the balloon (212) may also be referred to as one version of a tentacle for delivering a flowable material. In the illustrated version, the dual lumen (218) is non-linear and has a substantially S-shaped or curved distal end about which the balloon (212) is mounted. Substantially linear versions or other orientations for the dual lumen (218) are contemplated. With particular reference to the cross-sectional view of FIG. 14, the dual lumen (218) includes a saline delivery lumen (222) and an adjacent cement delivery lumen (224) in a parallel configuration. The saline delivery lumen (222) is fused at the distal end just proximal to the distal end and includes one or a plurality of apertures (216) that establish fluid communication with the internal cavity of the balloon (212). The saline delivery lumen (222) provides fluid communication between the access port (202) and the balloon (212) such that saline delivered through the access port (202) enters, fills, and expands the balloon (212). Similarly, saline withdrawn through the access port (202) correspondingly deflates the balloon (212). In the illustrated version, saline delivered through the access port (202) into the balloon (212) is used solely for balloon inflation and is not released into the vertebra or any other part of the body. However, saline may be released or delivered into a vertebral body, for example, to assist is clearing away cancellous bone from the cortical wall.

Although inflation of the balloon (212) is described with reference to saline, it will be appreciated that any suitable flowable material or fluid, which includes air or gases, may be used to inflate and/or deflate the balloon (212). For example, bone cement, biologic material, bone growth materials, bone fragments, bone paste, bone gel, saline, saline mixed with radiopaque additives, pressurized air, or combinations thereof may be utilized. The balloon (212) may be non-porous, semi-porous, or porous where, for example, a porous balloon filled with bone cement may ooze bone cement into a vertebral cavity during inflation.

It will be appreciated that the dual lumen (218) may have any suitable configuration and any suitable number of lumens passing entirely or partially therethrough. The dual lumen (218) may extend through the balloon (212) as illustrated or, alternatively, the dual lumen (218) may be adjacent or set apart from the balloon (212). The saline delivery lumen (222) and the cement delivery lumen (224) may be configured as separate lumens not retained within a single dual lumen (218). Generally, all lumens may be single lumen or multi-lumen tubing, where multi-lumen tubing may provide an advantageous drop in internal diameter by sharing a wall. Additional lumens may be provided, for example, for suction, irrigation, a guidewire, inflation of additional inflatable members or cement containers, or for tamping.

Still referring to FIGS. 10, 11, and 14, the cement delivery lumen (224) extends along the length of the dual lumen (218) and terminates in a distal aperture (226) at the distal end of the reduction apparatus (200). The cement delivery lumen (224) is in fluid communication with the access port (204) such that cement delivered through the access port (204) exits the apparatus (200) at the distal aperture (226). The access port (204) and cement delivery lumen (224) are configured to deliver bone cement, or any other suitable material, through the reduction apparatus (200) into a vertebral body cavity to, for example, restore the strength of the vertebra after fracture reduction. In the illustrated version, the access port (204) and the cement delivery lumen (224) are configured in such a manner that instruments, such as tamping instruments, cannot be inserted into the lumen (224); however, it will be appreciated that the access ports can be configured to accept tamping instruments, or the like, to facilitate expelling materials from within the lumens, packing materials into the vertebral body, and/or capping the access point to the vertebra after inserting filler material. Providing a separate port configured to accept a tamping, capping, or packing instrument is also contemplated.

Referring to FIGS. 10 and 11, in one version, the side lumen (220) is an elongate PET tube in fluid communication with the access port (206) that terminates in a delivery tentacle (214). In the illustrated version, there is a single delivery tentacle (214) made from PET that is integral and in fluid communication with the side lumen (220). With particular reference to the cross-sectional view of FIG. 14, the side lumen (220) may be bonded with a UV curable adhesive to the dual lumen (218) and the balloon (212), where both the dual lumen (218) and the side lumen (220) may be surrounded by an elongate sheath (210) that extends from the housing (208)

to just proximate the balloon (212). The dual lumen (218) may be bonded to the sheath (210) with cyanoacrylate. The delivery tentacle (214), which may be the portion of the side lumen (220) that projects from the sheath (210), can be bonded to the anterior side of the outer surface of the balloon (212) with UV curable adhesive. The delivery tentacle (214) includes a plurality of spaced apart apertures along the length of the tentacle through which cement is delivered into a vertebral cavity.

It will be appreciated that the illustrated lumens (218), (210) may be bonded or retained by any suitable means, such as the sheath (210), as illustrated, or any suitable adhesive. The delivery tentacle (214) and side lumen (220) may be a contiguous structure, as shown, or, alternatively, the delivery tentacle may be a separate component affixed, coupled, or otherwise attached to the side lumen (220). The side lumen (220) may be rigid and the tentacle (214) may be flexible, both may be flexible, or both may be rigid or semi-rigid. The delivery tentacle (214) further comprises one or a plurality of tentacles having any suitable configuration for the delivery of bone cement, dye, gas, filling agent, therapeutic agent, medicament, and/or any other suitable material. The delivery tentacle (214) may be provided with one or a plurality of apertures and/or may be constructed from a porous material for the delivery of fluid into a vertebra.

Referring to FIGS. 10, 11, and 13, in the illustrated version the balloon (212) is a non-porous PET structure, having a generally uniform wall thickness, positioned near the distal end of vertebral fracture reduction apparatus (200). The balloon (212) is coated with urethane and tungsten powder. Each end of the balloon (212) is bonded to the dual lumen (218) to form a fluid-tight seal during inflation. A length of the balloon (212) at each end is bound to the dual lumen with a strap to help maintain the integrity of the bond during inflation. The illustrated balloon (212) has a non-axisymmetric configuration and is not aligned about any linear axis. The balloon (212) defines a single internal cavity and is not compartmentalized. In the illustrated version, the balloon (212) does not have any internal restraints or external restraints that restrain expansion of the balloon. The proximal and distal regions of the balloon (212) have a greater width than the central portion of the balloon (212), and each end region tapers towards the coupling with the dual lumen (218). The balloon (212) is configured for fluid communication with the access port (202) and the saline delivery lumen (222) such that the balloon (212) may be inflated to reduce a vertebral bone fracture when expanded against cortical bone endplates.

The balloon (212) may be provided with any suitable features or elements configured to restrain, shape, or otherwise configured the balloon (212) including, for example, internal restraints, external restraints, varying wall thicknesses, bands, and/or variations in material. Although the balloon (212) is shown in a non-axisymmetric configuration, the balloon may have an axisymmetric configuration, or any other shape, and may be aligned along a linear axis. The ends of the balloon (212) may be tapered, as shown, or may be inverted or have any other suitable configuration. Providing a balloon having a uniform diameter along the length thereof is also contemplated. Any suitable partial or complete coating in one or a plurality of layers may be utilized including coatings that are lubricious, rough for trauma applications, radiopaque, anti-bone growth, non-adhesive, barium, bismuth, PET, materials embedded in PET, tungsten powder, tantalum, or combinations thereof Additionally, radiopaque coatings may be masked in certain sections to aid in visualization, measurement, trauma, placement, guidance, or the like. Any suitable region, band, design, marking, indicia, or writing may be masked or otherwise indicated for visualization.

Figure 15:
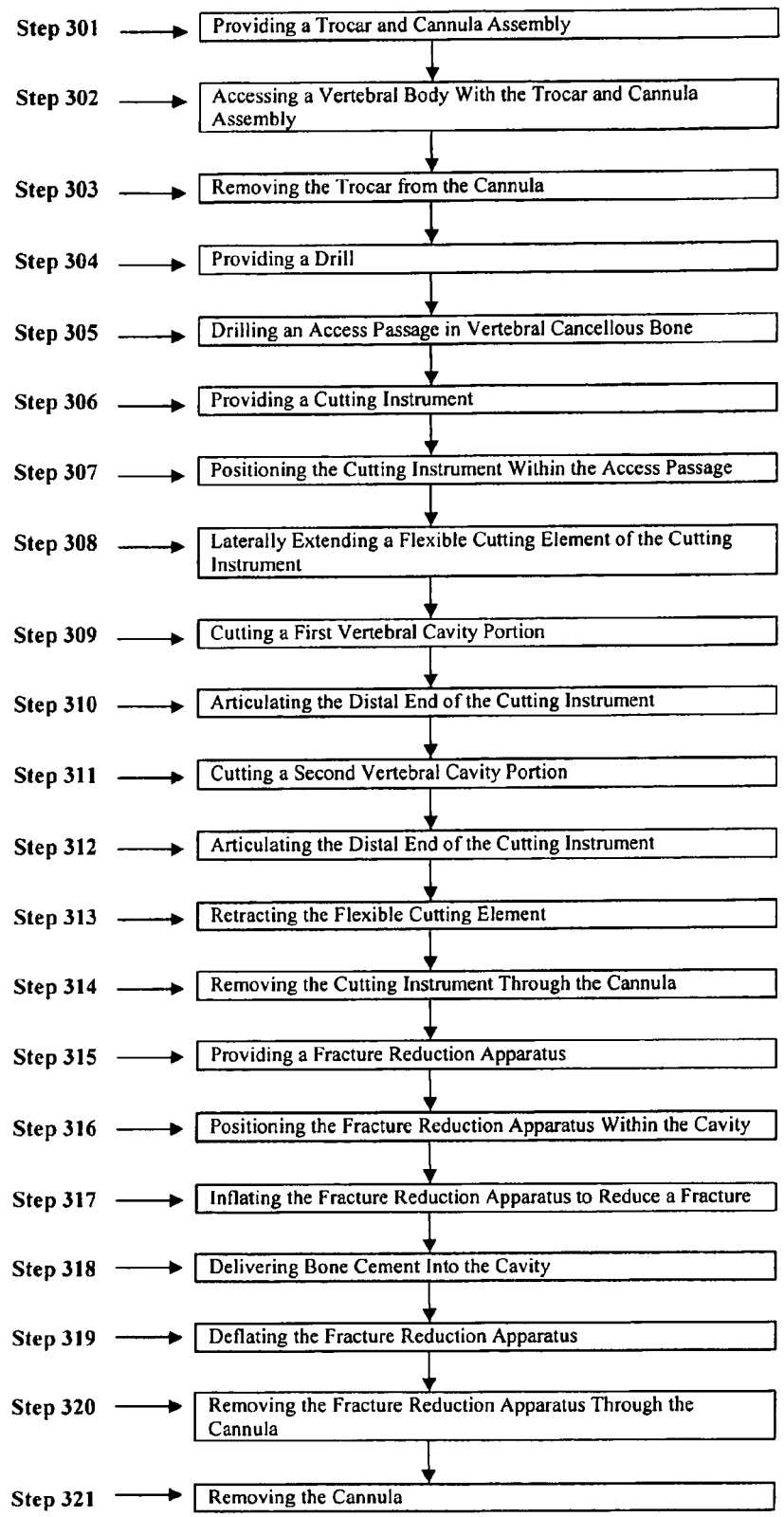
FIG. 15 depicts a flowchart of one version of a vertebral cavity formation and fracture reduction method.

Referring to FIG. 15, disclosed is one version of a method (300) for use of the vertebral cavity formation and fracture reduction system. The method comprises Providing a Trocar and Cannula Assembly Step (301) that includes providing, for example, the trocar and cannula assembly (10) described with reference to FIGS. 1-3. The method (300) comprises Accessing a Vertebral Body With the Trocar and Cannula Assembly Step (302). Step (302) includes making a small incision in the skin of a patient and inserting the trocar and cannula assembly (10) through the skin and adjacent a fractured vertebra with, for example, a trans-pedicular approach, a postero-lateral approach, or a trans-sacral axial bore approach. The vertebra is accessed initially, through, for example, the pedicle or cortical bone, with the first penetration member (24) of the trocar (12). The first penetration member (24) is configured with a small point at the distal end to facilitate the introduction of the trocar (12) into the pedicle, or other location, to allow for repositioning if needed, and to provide control in positioning the trocar. The small point of the first penetration member (24) is used to penetrate the pedicle until the second penetration member (26) abuts the pedicle. The larger diameter second penetration member (26) is then bored into the pedicle to form an access point sufficiently large for insertion of the cannula (14). After the access point is created by the trocar (12), the cannula (14) is retained within the access point to function as an instrument conduit for the duration of the procedure. Steps (301)-(303) are described with reference to a composite trocar and cannula assembly (10); however, it will be appreciated that any suitable trocar and/or cannula may be used in accordance with versions herein.

With the cannula (14) in place, the method (300) comprises Removing the Trocar from the Cannula Step (303), which includes withdrawing the trocar (12) proximally from the cannula by uncoupling the two-part handle (16) and withdrawing the first removable handle portion (18). Removing the handle portion (18) and the attached trocar (12) from the lumen of the cannula (14) leaves behind a hollow lumen through which a drill (40), shown in FIG. 4, a cavity formation instrument (100), shown in FIG. 5, a vertebral fracture reduction apparatus (200), shown in FIG. 10, and/or any other suitable instrumentation, may be inserted. Upon removal of the trocar (12), the cannula (14) is left in place within the vertebra where it will remain for the duration of the procedure. Other instruments that may be inserted include a backup cement delivery tube, suction, a biopsy device, a camera, a scope, a bone remover, or a cement stopper.

The step of Providing a Drill Step (304) includes providing a passage creating instrument, such as the drill (40), which is described with reference to FIG. 4. The step of Drilling an Access Passage in Vertebral Cancellous Bone Step (305) includes inserting the passage creating instrument or drill (40) into the cannula (14) until the drill (40) abuts vertebral bone. In one version, the drill bit (46) of the drill (40) is then manually rotated to form a substantially linear cylindrical passage into the vertebral cancellous bone up to the anterior cortex. The depth of the passage is measured by the markings (50) on the body (42) of the drill (40) to guide the surgeon in controlling the creation of the passage. In one version, the handle (44) of the drill (40), which projects proximally from the second handle portion (20) of the cannula (14), is manually rotated by the surgeon's hand via the grip (48) to form the desired passage. Step (305) further includes removing the drill (40) from the cannula (14) after creation of the passage. It will be appreciated that manual operation of various instrumentation described herein can be performed with a motor or by other electrical or mechanical means.

The step of Providing a Cutting Instrument Step (306) includes providing a cavity formation instrument or device such as the cavity formation instrument (100) described with reference to FIGS. 5-9. The step of Positioning the Cutting Instrument Within the Access Passage Step (307) includes inserting the cavity formation instrument (100) through the lumen of the cannula (14) into the passage created by the drill (40). During insertion, the cavity formation instrument (100) is maintained in a linear position where the end effector (106) is aligned with the first linear axis A-A. The flexible cutting element (118) is in the fully retracted position to minimize the width of the end effector (106) during insertion. The depth and placement of the cavity formation instrument (100) may be monitored via fluoroscope along with depth markings to properly position the end effector (106) within the access passage of the vertebra. In one version, the end effector is positioned such that it is entirely within the cancellous bone volume of a single vertebra. It will be appreciated that methods described herein may also be used for tissue cavity formation, orthopedic cavity formation, spinal cavity formation, vertebral cavity formation, discectomies, or other orthopedic or medical procedures.

The step of Laterally Extending a Flexible Cutting Element of the Cutting Instrument Step (308) includes laterally extending the cutter (118) away from the end effector (106). In one version, the cutter (118) is laterally extended by manually rotating the rotational member (112) in a first direction. Manual rotation of the rotational member (112) operates as a jack screw to urge the shaft (128) distally. Distal translation of the shaft (128), which is coupled with the cutter (118) via the junction member (132), urges the cutter (118) outward through the aperture (134). Because, in the illustrated version, the cutter (118) is fixed at one end to a proximal portion of the end effector (106), the cutter (118) is expanded outwardly to form an arcuate shape as the shaft (128) is urged distally. Step (308) includes laterally extending the arcuate shape of the cutter (118) a desired distance as determined by fluoroscope or by resistance from the access passage.

The step of Cutting a First Vertebral Cavity Portion Step (309) includes forming a cavity within the cancellous bone of a vertebra using the cutting instrument (100). Following Step (308) where the cutter (118) is partially laterally extended, the end effector (106) may be rotated about the first linear axis A-A to cut cancellous bone tissue. In one version, the cavity is formed by manually rotating the rotational member (114), which correspondingly rotates the shaft (128) and end effector (106) to cut into cancellous bone. The cavity formed in Step (309) may be generally axisymmetric about the first linear axis A-A. The cavity may have a greater width than the drilled access passage. In one version, the Steps (308) and (309) are performed simultaneously to extend the cutting element (118) while rotating the end effector (106) to form a cavity. Although described with reference to forming a vertebral cavity, it will be appreciated that a cavity forming instrument described in accordance with methods herein may be used in any suitable orthopedic or medical application such as, for example, to form cavities in long bones or in cardiovascular applications for plaque removal. Other applications include vertebral disc applications, neurosurgery, interventional radiology, and pain management.

Step (309) further includes extending the cutter (118) laterally at increments to form successively larger cavities. The cutter (118), may be extended as described with reference to Step (308), is used to cut a portion of a cavity as described above. In one version, the cutter (118) is then incrementally extended radially outward via rotation of the rotational member (112). The rotational member (114) is then rotated to form a successively larger cavity. The incremental extension of the cutter (118) with subsequent cavity formation via the rotational member (114) is repeated a sufficient number of times to create the desired cavity. A suitable cavity size is determined via fluoroscope. During cavity creation, as the cancellous bone is cut it may be allowed to collect, gather, or pool within the vertebra, it may be compacted against the cortical wall, and/or it may be removed from the vertebra. A suction device may be provided to remove pieces of bone and/or a compaction device may be provided to compact bone against the cortical wall to clear cancellous bone from the cavity.

The step of Articulating the Distal End of the Cutting Instrument Step (310) includes articulating the end effector (106) of the cutting instrument (100) within the cavity formed in accordance with Step (309) such that it is offset from the first linear axis A-A. The end effector may be offset such that it is aligned with a second linear axis such as axis B-B. The articulation may occur at one or a plurality of articulation points or regions, where the end effector (106), for example, may be articulated such that it is offset a first distance from the axis A-A. The first distance may be achieved by pivoting the end effector (106), bending the end effector (106), or otherwise articulating the end effector (106) such that it is offset, pivoted, or spaced apart from the axis A-A. Step (310) includes partially retracting the cutter (118) such that it is adjacent the end effector (106) prior to articulation. The end effector (106) may then be articulated by rotating the distal rotational member (110) in a first direction as described herein.

In one version, articulation in accordance with Step (310) is accomplished by incrementally articulating the end effector (106) toward the opposite side of the intervertebral space of the vertebral body. The rotational member (110) is rotated in a first direction to urge the end effector (106) such that it is incrementally offset from the first linear axis A-A. The rotational member (114) is then rotated to increase the size of the cavity to provide more space for the articulation of the end effector (106). The rotational member (110) is again rotated in the first direction to further articulate the end effector (106) incrementally before again rotating the end effector via the rotational member (114). The incremental articulation of the end effector (106) with subsequent cavity formation via the rotational member (114) is repeated a sufficient number of times, as needed, until the end effector (106) is sufficiently articulated. Alternatively, rotation and articulation may be performed simultaneously. The end effector (106) is properly guided by the surgeon to the central position via fluoroscope. Articulating the end effector (106) towards the opposite side of the vertebral body may allow a cavity to be formed that exposes the cortical endplates for direct contact with the balloon (212) during expansion to reduce a vertebral compression fracture. Once positioned, the end effector (106) may be aligned along a second linear axis B-B angled away from the first linear axis A-A of the insertion tube (104).

The step of Cutting a Second Vertebral Cavity Portion Step (311) includes expanding the cavity portion formed in accordance with Step (309), for example, to expose regions of cortical bone within the intervertebral space. The second cavity portion is formed, in one version, by laterally extending the cutter (118) and rotating the cutter (118) in the stepwise manner as described in accordance with Steps (308) and (309) to expose the end plates of the vertebra. Alternatively, these can be actuated simultaneously. As with Steps (308) and (309), the cutter (118) may be guided via fluoroscope. Specifically, the formation of the second cavity portion may form a central cavity that exposes the endplates of the vertebral cortical bone that will serve as the foundation for expansion of the fracture reduction balloon (212).

In one version, as the endplates are exposed, the cutter (118) may form a pocket within the cancellous bone adjacent the anterior wall of the vertebral body. When a fracture reduction procedure is performed with the patient lying face down, there is a natural tendency for cut cancellous bone to be drawn away from the intervertebral space into the anterior pocket of the cavity. In this manner, the anterior pocket of the cavity may be used as a cancellous bone reservoir that obviates the need for bone compaction or bone removal to access the end plates. Step (311) comprises cutting cancellous bone away from the endplates of a vertebra and allowing the cut cancellous bone to collect in the anterior pocket of the cavity. Cutting away cancellous bone, rather than compacting the cancellous bone, provides for an exposed cortical surface that may be more responsive to more predictable compression forces. Removing as much cancellous bone as possible from the intervertebral body adjacent the endplates may increase the predictability and control of the procedure.

Although a method of cutting and collecting cancellous bone is described, it will be appreciated that cancellous bone may be removed, pooled, condensed, and/or compacted to form a cavity or cavity portion in accordance with versions herein. For example, cutting away a portion of the cancellous bone and then compacting a thin region of cancellous bone may act as a seal within the vertebral body to prevent the leakage of bone cement or other fluid. By cutting away a first portion of cancellous bone, prior to compacting a second region of cancellous bone, sufficient cancellous bone may be removed such that a fracture reduction device is sufficiently adjacent the cortical bone of the vertebra to effectively reduce a fracture. Thus, numerous techniques may be combined in forming a desired cavity. Multiple accessing, cutting, tamping, compaction, stoppering, curing, removal, suction, and/or expansion devices may be inserted or otherwise used in any suitable manner or order.

The step of Articulating the Distal End of the Cutting Instrument Step (312) includes articulating the end effector (106) of the cutting instrument (100) in the return direction until it is linearly aligned with the first linear axis A-A. The end effector (106) is articulated into alignment by rotating the distal rotational member (110) in a second direction. In this manner, the cutting instrument (100) may be returned to its pre-insertion linear configuration such that it can be easily removed through the cannula (14). The step of Retracting the Flexible Cutting Element Step (313) includes withdrawing the cutter (118) through the aperture (134) by rotating the rotational member (112) in a second direction. In this manner, the cutter (118) is returned to its pre-insertion retracted configuration such that it can be easily removed through the cannula (14). The step of Removing the Cutting Instrument Through the Cannula Step (314) includes removing the cutting instrument (100) through the cannula after the cutter (118) has been retracted and the end effector (106) has been brought into linear alignment with the insertion tube (104). In one version, the cannula (104) is left in place during all Steps in which the cutting instrument (100) is utilized. It will be appreciated that any suitable number of cavity formation instruments having any suitable configuration may be inserted through the cannula (14). For example, cavity formation devices having a plurality of articulations or joints and/or varying degrees of articulation may be utilized. Although the end effector (106) is described as retaining a substantially linear configuration, it will be appreciated that the end effector (106) may have any suitable shape, such as a curved shape, or be deformable such as, for example, from a substantially linear shape to a curved shape if made from a shape memory alloy such as a nickel-titanium alloy.

The step of Providing a Fracture Reduction Apparatus Step (315) includes providing a fracture reduction apparatus such as the fracture reduction apparatus (200) described with reference to FIGS. 10-14. It will be appreciated that Step (315) is described with reference to the reduction of vertebral fractures by way of example only and may be used in any suitable tissue application. The step of Positioning the Fracture Reduction Apparatus Within the Cavity Step (316) includes inserting the fracture reduction instrument (200) through the lumen of the cannula (14) into a cavity created by, for example, the cutting instrument (100). Prior to insertion, the balloon (212) may be pleated and folded in a folding machine or otherwise be provided with a reduced size. The folding machine includes two separate sets of jaws having a plurality of fingers each, where the first set of jaws heats and pleats the balloon (212) and the second set of jaws folds the balloon (212) by wrapping it around the central lumen (218). During insertion, the fracture reduction apparatus (200) is maintained in a deflated position to minimize the width of the balloon (212) during insertion. In one version, the flexibility of the tentacle (214) during insertion allows for the reduced diameter tentacle (214) to be inserted through a relatively narrow access passage. The flexibility of the tentacle (214) then allows for greater expansion of the tentacle (214) after insertion. The depth and placement of the fracture reduction apparatus (200) are monitored via fluoroscope and with depth markings to properly position the balloon (212) within the cavity of the vertebra.

After insertion of the fracture reduction instrument, the substantially S-shaped or curved distal end of the dual lumen (218) shown in the illustrated version is projected into the vertebral cavity such that the balloon (212) is centrally located within the cavity. In one version, the balloon (212) is positioned such that, upon expansion, the walls of the balloon press against the exposed endplates of the vertebra after cancellous bone has been removed. Other versions may compact substantial or minimal amounts of cancellous bone. The balloon (212) may be constructed from flexible but substantially inelastic PET such that the balloon (212) expands only to a predetermined shape regardless of the level of inflationary pressure. The balloon (212) may be configured to expand against the cortical endplates to reduce a vertebral fracture, but not to penetrate the anterior pocket of the cavity into which the cancellous bone may be collected. Thus, in one version, the vertebral endplates are expanded to reduce the vertebral fracture without compacting or removing cancellous bone. Alternative versions may incorporate removing and/or compacting cancellous bone.

The step of Inflating the Fracture Reduction Apparatus to Reduce a Fracture Step (317) includes inflating the fracture reduction element (200), for example, against the exposed endplates of a vertebra to reduce a fracture. In one version, the balloon (212) is expanded uniformly with the introduction of a flowable material, such as saline, via the access port (202). In one version, the flexible but inelastic PET balloon (212) is configured to expand against the endplates of the vertebra without expanding to fill the entire cavity. In this manner, the bone fracture is reduced without compacting the bone retained within the anterior pocket of the cavity. After being positioned adjacent the endplates of the vertebra in accordance with Step (316), the balloon (212) is inflated with a syringe by introducing saline solution through the access port (202) and saline delivery lumen (222). The inflation of the balloon (212) corresponds to the volume of saline delivered through the syringe. A surgeon determines sufficient inflation by viewing the fracture reduction apparatus (200) under a fluoroscope and by monitoring the pressure gauge. Because the balloon (212), in the illustrated version, is constructed from flexible but substantially inelastic PET, the balloon expands only to its predetermined shape regardless of the level of inflationary pressure. The balloon (212) is configured to expand against the cortical endplates to reduce the fracture, but not to penetrate the anterior pocket of the cavity into which the cancellous bone has collected. Thus, in one version, the vertebral endplates are expanded to reduce the fracture without compacting or removing cancellous bone.

It will be appreciated that the balloon (212) may, alternatively, have an elastic configuration configured to fully fill a cavity, internal or external restraints to define the shape of the balloon, any suitable shape, any suitable radiopaque marker, any suitable surface effect or coating, any suitable number of chambers, compartments, or layers, and/or any suitable combination of materials or wall thicknesses. Although the balloon (212) has been described with reference to vertebral fracture reduction procedures, it will be appreciated that the methods described herein may be useful in other medical procedures such as orthopedic or cardiovascular applications. The balloon (212) may be used to compact cancellous bone to form a cavity and/or to form a seal around cortical bone to prevent bone cement or fluid leakage. The balloon (212) may be filled or inflated with any suitable material such as saline, bone cement, gas, dye, and/or any other fluid and may have a porous or non-porous surface. In one version the balloon (212) is permanently implantable where, for example, the balloon is inflated with bone cement and left within the vertebra.

The step of Delivering Bone Cement Into the Cavity Step (318) includes delivering any suitable flowable material, such as bone cement, fluid, air, gas, medicament, bone paste, bone pieces, bone growth factor, or the like, through the cement delivery lumen (224) and the delivery tentacle (214) via access ports (204) and (206), respectively. Flowable material is delivered through the access ports (204) and (206) with a syringe that is manually plunged. Following Step (317), where the balloon (212) is inflated, the flowable material is delivered through the tentacle (214) to fill a portion of the cavity. As the cavity becomes filled with bone cement, or any other suitable flowable material, the balloon (212) may be gradually deflated in accordance with Step (319) to allow bone cement delivered through cement delivery lumen (224) to fill the void within the intervertebral space. Bone cement delivered through the tentacle (214) may be allowed to fully set or only partially set prior to delivering cement through delivery lumen (224). In one version, flowable material may delivered via the cement delivery lumen (224) and/or the delivery tentacle (214) prior to inflation of the balloon (212), where, for example, bone cement may be delivered via the tentacle (214) prior to inflation and, upon inflation, the bone cement is urged into any cracks that may be present in cortical bone.

Step (318) further includes delivering multiple successive layers of a material, such as bone cement, to the inner surface of a vertebral cavity. For example, a layer of bone cement may be delivered through the tentacle (214) and allowed to set for a predetermined period of time. Multiple successive layers of bone cement, therapeutic materials, fluids, or the like, may then be provided within the vertebral cavity. One or a plurality of layers or coatings may be delivered with the fracture reduction element (200) and/or other delivery instruments.

The step of Deflating the Fracture Reduction Apparatus Step (319) includes partially deflating the fracture reduction apparatus (200) such that bone cement can be delivered into the cavity. The balloon (212) of the fracture reduction apparatus (200) is deflated by withdrawing the syringe associated with access port (202) to draw fluid out of the balloon (212). Removing fluid with the syringe decreases the volume of saline within the balloon and creates a vacuum within the balloon that helps with retraction. Step (319) further includes fully deflating the balloon after a sufficient amount of bone cement has been delivered in accordance with Step (319). Step (319) further comprises mechanically wrapping the balloon (212).

The step of Removing the Fracture Reduction Apparatus Through the Cannula Step (320) includes removing the fracture reduction apparatus (200) after the balloon (212) has been substantially deflated and the cavity has been filled with bone cement. While the balloon (212) is mostly removed from the vertebra, bone cement is delivered through the cement delivery lumen (224) to fill the cavity. In this manner, the bone cement is able to fill the cavity while the vertebra is being compressed outwardly to cement the vertebra with the fracture reduced. The fracture reduction apparatus (200) is then removed through the cannula (14). The step of Removing the Cannula Step (321) includes removing the cannula (14) from the vertebral body after the vertebral fracture has been reduced and bone cement injected. Step (321) includes removing the cannula (14) from the patient's body. Step (321) may further include inserting a stopper device through the cannula (14), prior to removal of the cannula, that prevents bone cement or filler material from escaping from the vertebral cavity before beginning to set. Once the material is partially set, the stopper device and cannula (14) may be removed.

FIGS. 16-24 depict alternative versions of the end effector (106) of the cutting instrument (100), shown in FIGS. 5-7 and 9, utilizing a generally band-shaped cutting element. Alternative versions described herein utilize shape-changing cutting elements configured to form or modify cavities in either hard or soft tissue including, for example, cancellous bone within a vertebra. The shape-changing behavior enables the cutting instrument (100) to be inserted into tissue through a relatively small access opening to form a tissue cavity having a diameter larger than the diameter of the access point. Thus, versions described herein may be particularly useful in minimally invasive surgery, and may be used for at least the following specific applications, among others: (1) treatment or prevention of bone fracture, (2) joint fusion, (3) implant fixation, (4) tissue harvesting (especially bone), (5) removal of diseased tissue (hard or soft tissue), (6) general tissue removal (hard or soft tissue), (7) vertebroplasty, and (8) kyphoplasty. Tissue cavities created in accordance with versions described herein may be of any suitable size, shape, or configuration including a spherical cavity, a hemispherical cavity, a linear cavity, a groove, a channel, a cavity having varying geometries, such as an upper hemispherical chamber and a lower linear cavity, or any other suitable cavity configuration. Articulation of the alternative versions of the end effector (106) may allow for numerous cavity configurations to be created along multiple axes and/or planes.

Figure 16:
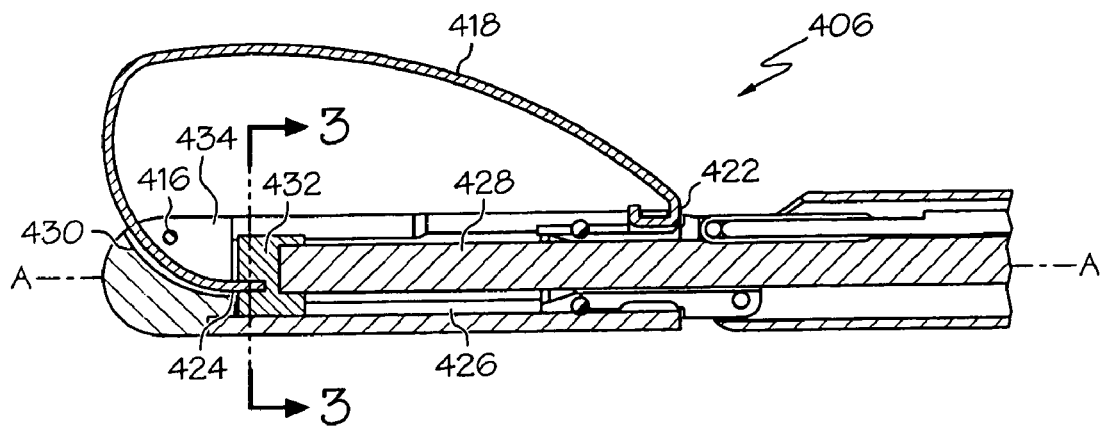
FIG. 16 depicts a longitudinal, cross-section view of a medical device having an extendable cutting member coupled with a transition member shown in an extended position.

FIG. 16 shows one version of an end effector (406) that may used, for example, with the cutting device (100) shown in FIG. 5. It will be appreciated that the term "end effector" can refer, generally, to the working end of the cutting instrument or to an identifiable component of the cutting instrument. For example, the end effector (406) may be coupled with the insertion tube (104), shown in FIG. 5, or may be part of a contiguous insertion tube. The end effector (406) includes a shaft (428), a flexible cutting element (418), a transverse member (416), such as a guide, pin, or catch, and a transition member (432). In the illustrated version, the shaft (428) has a longitudinal axis A-A and a generally circular cross-section. It will be appreciated that any suitable cross-section, such as a generally square cross-section, a generally elliptical cross-section, or a polygon cross-section are contemplated. In the illustrated version, the end effector (406) includes an aperture (434), where the flexible cutting element (418) is configured to be housed or retained at least partially within the end effector (406).

In the illustrated version, the flexible cutting element (418) is formed from a flexible material, such as stainless steel, and is coupled at a first end (422) to the end effector (406) at about the proximal end of the aperture (434). The flexible cutting element (418) is coupled at a second end (424) to a distal face of the transition member (432). Couplings may be laser welds or any other suitable connection. The flexible cutting element (418) may be coupled at or near the proximal end of the end effector (406), where a portion of the flexible cutting element (418) may be curled under the proximal lip of the end effector (406), as is shown with reference to end effector (106) in FIG. 9, to form a living hinge that diminishes the stress placed upon the flexible cutting element (418) when deformed. The flexible cutting element (418) may be a flexible band, a cylinder, a ribbon, a serrated element, or have any other suitable configuration. The flexible cutting element (418) may have a uniform cross-section or varying cross-section.

The transition member (432) is configured to translate along the axis A-A such that axial motion relative to the end effector (406) may be translated to the flexible cutting element (418) to project the flexible cutting element (418) laterally through the aperture (434). The transition member (432) may be slidable along a track (426) of the end effector (406) such that rotational movement of the transition member (432) relative to the end effector (406) is restricted. For example, referring to FIG. 18, which is a cross-sectional view of the end effector (406) taken along line 3-3, the transition member (432) may have a wide base (436) to prevent such rotational movement. The transition member (432) may have any suitable shape configured to restrict rotational movement relative to the end effector (406) while allowing axial movement such that the flexible cutting element (418) may be deformed or laterally extended.

Still referring to FIG. 16, the shaft (428) is distally coupled to a proximal face of the transition member (432) and is connected proximally to an actuator, such as those described with reference to the cutting device (100) shown in FIGS. 5-9. The shaft (428) is configured to actuate the transition member (432) proximally and distally to deform the flexible cutting element (418). A rigid or flexible shaft (428) may extend along the axis A-A and may be fixedly coupled with the transition member (432). Proximally, the shaft (428) may be associated with any suitable actuator configured to provide axial movement including, for example, actuators and actuation mechanisms described in co-pending U.S. patent application Ser. No. 11/600,313, which is herein incorporated by reference in its entirety. Such actuators may include knobs, slides, T-rails, spools, gear assemblies, triggers, manual actuation, electrical actuation, or the like.

In FIG. 16, the flexible cutting element (418) is shown in an expanded position configured to form a cavity in, for example, cancellous bone tissue of a vertebra. The expanded position may be formed by distally actuating the shaft (428) with an actuator such that the transition member (432) urges the flexible cutting element (418) against a ramp or inclined portion (430) that may be integral with the end effector (406). The inclined portion (430) may be integrally formed with the end effector (406), may be an insert, or may otherwise be suitably configured to guide the flexible cutting element (418) laterally through the aperture (434) as axial compression force is applied along the axis A-A. As the shaft (428) is actuated axially in a generally distal direction, the flexible cutting element (418) will correspondingly deform laterally through the aperture (434). The transition member (432) may be actuated distally until a stop (435) is abutted along the track (426).

Figure 23:
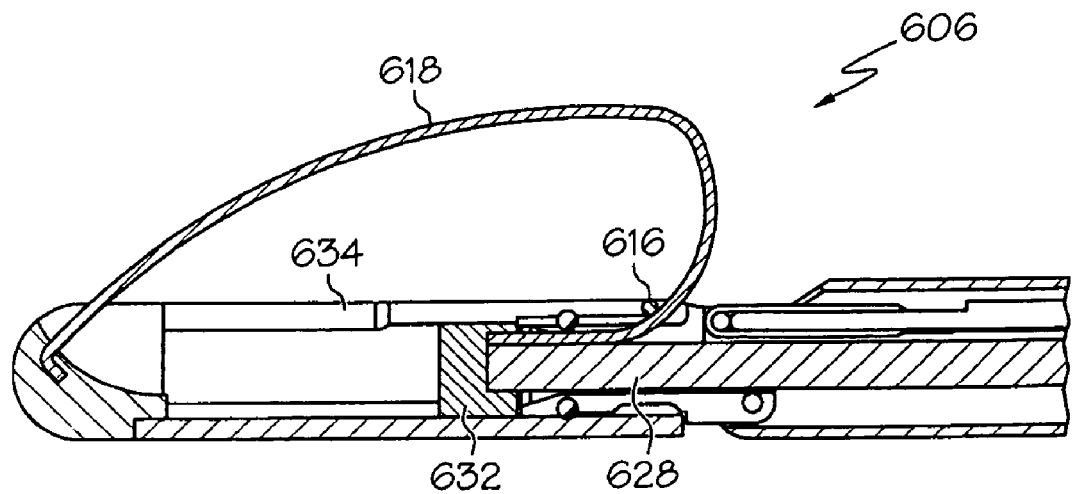
FIG. 23 depicts a longitudinal, cross-section view of an alternate version of a medical device having an extendable cutting member coupled with a shaft member shown in an extended position.

In one version, the flexible cutting element (418) is configured to extend from the proximal end to the distal end, or past the distal end, of the end effector (106), where the working length of the cutting element (418) may comprise substantially the full length of the end effector (406). A long working length may increase the cutting effectiveness and efficiency of the cutting element (418). Wrapping or curling one end of the flexible cutting element (418) around the proximal end of the end effector (406), such as illustrated in FIG. 16, may maximize the working length of the cutting element (418) while also providing a living hinge that biases the cutting element (418) outward. The flexible cutting element may also be curled around a portion of the distal end of the end effector as shown in FIG. 23.

When extended laterally, partially or fully, the flexible cutting element (418) may be used to form a cavity by rotating the end effector (406). The end effector (406) may be rotated by a second actuation member such as, for example, the rotational member (114) of the cutting device (100) shown in FIG. 5. For example, the transition member (432) may be configured such that rotation is translated to the end effector (406), where rotation of the transition member (432) via the shaft (428) correspondingly rotates the end effector (406). In such a manner, the shaft (428) may be used to deform the flexible cutting element (418) and to rotate the flexible cutting element (418) to form a cavity. Rotational and axial motion of elements of the cutting device (100) may be provided by one or a plurality of actuators as described herein.

Figure 17:
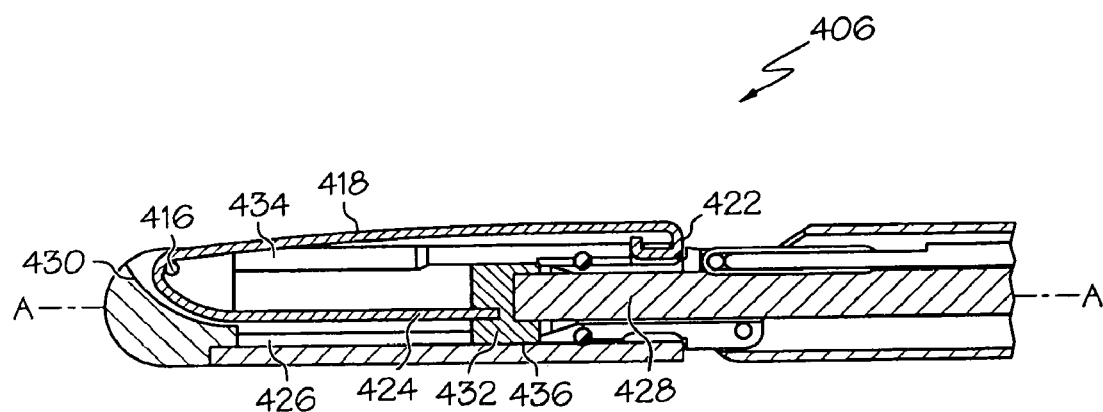
FIG. 17 depicts a longitudinal, cross-section view of the extendable cutting member of FIG. 16 shown in a retracted position.
Figure 18:
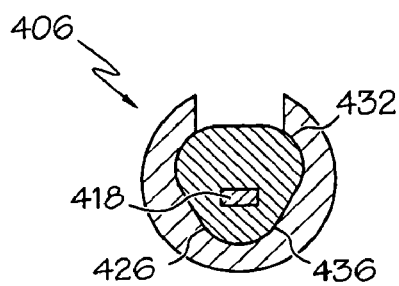
FIG. 18 depicts a transverse, cross-section view of the medical device of FIG. 16 taken along reference line 3-3 showing the transition member.

Referring to FIG. 17, the flexible cutting element (418) of the end effector (406) may be deformed to a retracted position for insertion, for example, into a pilot hole in a vertebra, or for removal through a minimally invasive insertion point or cannula upon completion of a procedure as described, for example, with reference to FIG. 15.

In the retracted position, the shaft (428) and the transition member (432) are urged in a generally proximal direction such that the flexible cutting element (418) is withdrawn through the aperture (434). In the illustrated version, the flexible cutting element (418) is drawn about a catch or transverse member (416) to achieve a substantially controlled and uniform retraction. When retained against the transverse member (416), the flexible cutting element (418) may be tensioned in the retracted position until the shaft (428) is actuated distally. The transverse member (416), in the illustrated version, is a cylindrical bar fixed to the sides of the end effector (406) perpendicular to the axis A-A. The transverse member (416) is configured such that the flexible cutting element (418) is slidable thereabout. The transverse member (416) is one version of a catch that may have any suitable shape, where the transverse member need not be directly perpendicular to the axis A-A. The transverse member (416), particularly when configured as illustrated in FIG. 8, may help prevent the cutting element (418) from buckling during actuation. In particular, the bottom curved surface of the transverse member may resist buckling.

Figure 19:
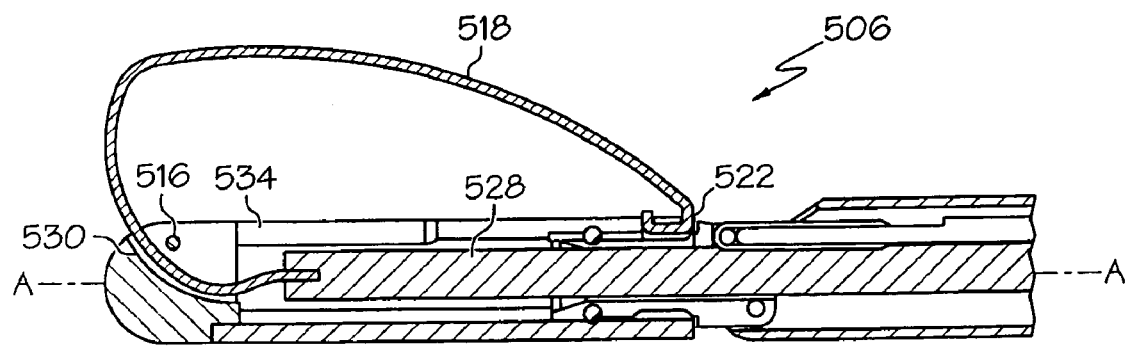
FIG. 19 depicts a longitudinal, cross-section view of an alternate version of a medical device having an extendable cutting member coupled with a shaft member shown in an extended position.
Figure 20:
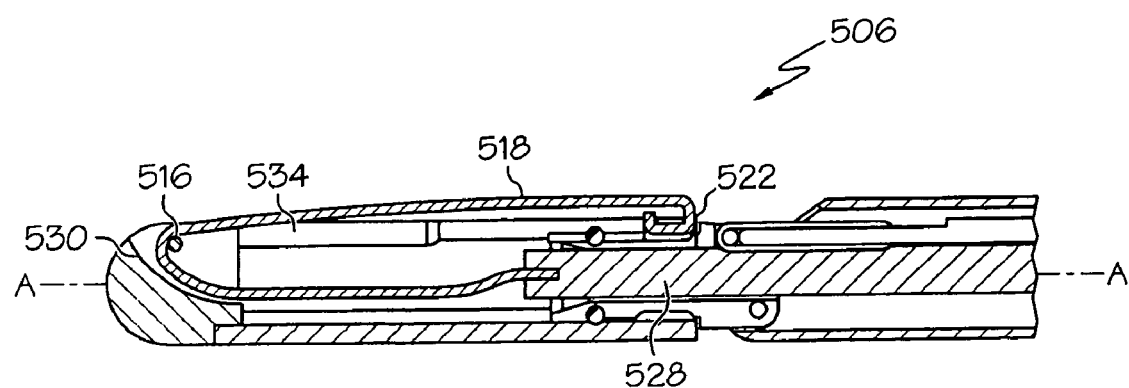
FIG. 20 depicts a longitudinal, cross-section view of the extendable cutting member of FIG. 19 shown in a retracted position.

Referring to FIGS. 19-20, an alternate version of an end effector (506) is shown where the flexible cutting element (518) is coupled directly with the shaft (528). The flexible cutting element (518) may be deformed as described above; however, the shaft (528) may be rotatable relative to the end effector (506). Rotation of the end effector (506) may be achieved via the shaft (528) by rotating the shaft (528) until the flexible cutting element abuts the aperture (534) and further rotation of the flexible cutting element correspondingly rotates the end effector (506). It will be appreciated that the flexible cutting element (518) may be contiguous with the shaft (528).

Figure 21:
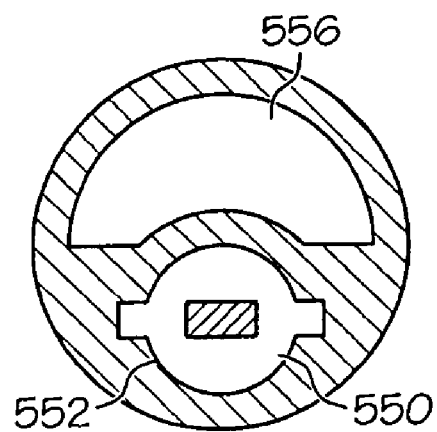
FIG. 21 depicts a transverse, cross-section view of a medical device taken along reference 3-3 of FIG. 16 illustrating an alternate version of a transition member.
Figure 22:
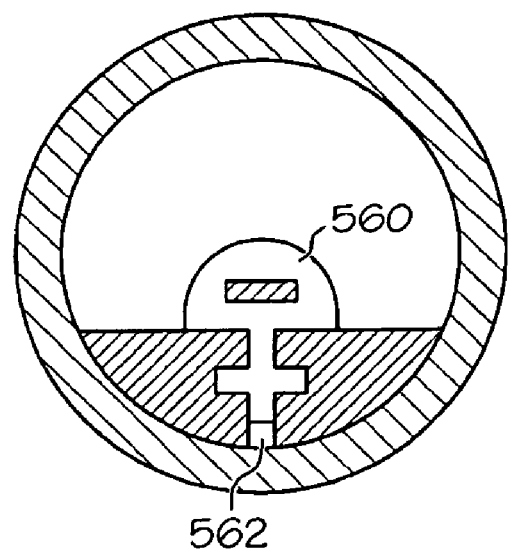
FIG. 22 depicts a transverse, cross-section view of a medical device taken along reference 3-3 of FIG. 16 illustrating an alternate version of a transition member.

Referring to FIGS. 21-22, alternate versions of transition elements, taken along a line similar to that of line 3-3 of FIG. 16, are shown in cross-section. It will be appreciated that versions of the transition elements described herein may have any suitable configuration such as a toothed cylindrical transition element (550) guided within a corresponding keyed channel (552) of an end effector. As shown the transition element (550) may track within a chamber or lumen (554) separate from an adjacent chamber or lumen (556) which may be used, for example, as a suction or irrigation channel. Referring to FIG. 22, the transition element may be a toothed projecting transition element (560) configured to slide within a corresponding channel (562). Any suitable slide or tracking configuration is contemplated. It will be appreciated that the blade or cutting member may also be keyed or otherwise configured to track within the end effector.

Figure 24:
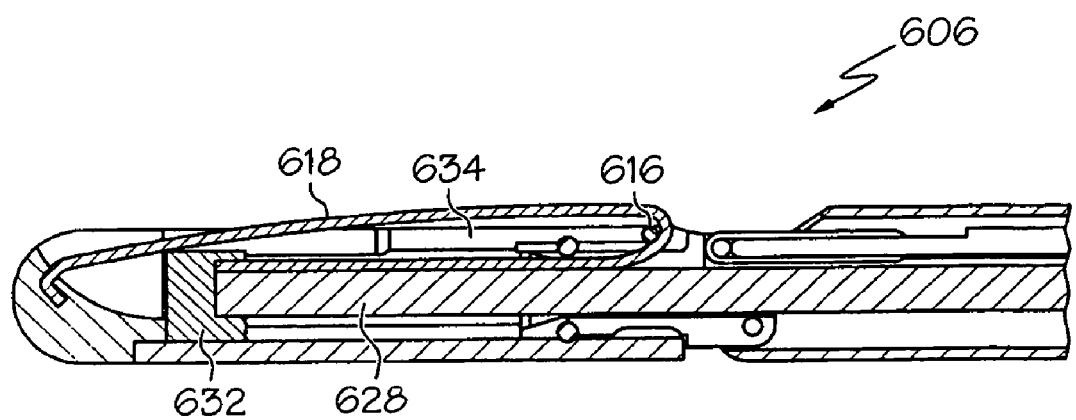
FIG. 24 depicts a longitudinal, cross-section view of the extendable cutting member of FIG. 23 shown in a retracted position.

FIGS. 23-24 illustrate an alternate version of an end effector (606) wherein proximal actuation of a transition member (632) with a shaft (628) expands a flexible cutting element (618) through an aperture (634) in the end effector (606). One end of the flexible cutting element (618) may be fixed to the distal end of the end effector (606) and the other end may be coupled with the transition member (632). With reference to FIG. 24, distal actuation of the transition member (632) draws the flexible cutting element (618) into contact with a guide pin (616), or other restrictive member, such that the flexible cutting element (618) is retracted into the end effector (606). It will be appreciated that any suitable configuration using a guide pin, or other guide member, is contemplated. Altering the position of the guide pin or member, such as towards the proximal or distal ends of the aperture, may alter the arcuate shape of the flexible cutting element and provide various desirable cutting shapes for medical procedures. As has been described herein, the end effector (606) may be articulated, actuated, and/or rotated by any suitable means such as, for example, the cutting device (100), shown in FIG. 5, a T-handle, or a power drill.

Version of the flexible cutting element may have a bias toward a "remembered" shape, be configured from a material having a thermal response, have a curvilinear shape when expanded, have a waveform configuration when expanded, or may otherwise be suitably configured. The memory retention aspects of a number of materials, such as Nitinol or stainless steel, allow for a wide range of possible configurations that are contemplated. Shape may be determined or varied depending on the hardness, material, response to temperature, flexibility, and/or other properties of the cutting elements provided.

For example, a first cavity portion may be created with a flexible cutting element having a first configuration. After completion of the first cavity portion, the flexible cutting element may be changed, deformed, or transitioned to a second configuration to change or increase the size of the first cavity to form a second cavity. It is contemplated that a user may alternate between shapes, configurations, and directions while creating a cavity without removing the cavitation device from the vertebral body. Configurations from Nitinol, for example, may be predetermined such that a user may select a predictable shape from a selection such that the user knows precisely which shape is being used to cut tissue. It will be appreciated that the shapes may be discreetly selectable configurations or, in an alternate version, may be points along a continuum that may be selected during or prior to a procedure. Providing a plurality of selectable configurations and/or allowing a user to adjust the configurations of the cutting element may permit more precise cavity creation or modification.

Versions of the flexible cutting element may be configured, articulated, or manipulated into any suitable shape such as, for example, an arcuate shape, a plateau shape, a curvilinear shape, a coiled shape, a helical shape, a laterally extended shape, a convex shape, a concave shape, a linear shape, and/or a sinusoidal or wave-shape. The shaft portion may be integral and contiguous with the flexible cutting element or may be a more clearly defined or discreet actuation member coupled with the flexible cutting element. The distal end of the flexible cutting element may be permanently fixed to an insertion tube, such as with a laser weld, such that the distal end remains static as the shaft is tensioned, rotated, compressed, articulated, and/or otherwise moved to change the flexible cutting element from a first shape to a second shape. The shaft and/or the insertion tube may be rotated in a clockwise and/or counterclockwise direction to form or modify a desired cavity.

In addition to being rotatable or movable in one or a plurality of directions, the flexible cutting elements may be provided with one or a plurality of surface effects to create different cutting effects. Multiple cutting edges or surface effects may be combined in a single flexible cutting element to affect tissue differently depending upon the direction of cut. The term "surface effect" shall refer to any geometry, feature, projection, texture, treatment, edging, sharpening, tapering, material type, hardness, memory retention, heat treating, response to heat, roughness, smoothness, sharpness, shape, and/or configuration of one or a plurality of surfaces, faces, edges, points, or the like, of the flexible cutting element or any other component of a cavitation device. Any suitable surface effect is contemplated including, but not limited to, serrations, waves, convexities, concavities, edging, points, sharpened edges, smooth edges, rounded edges, flat edges, hardened edges, or combinations thereof It is further contemplated that a first surface effect may be provided on a first cutting surface and a second surface effect may be provided on a second cutting surface of a flexible cutting element such that varying the direction of rotation varies the type of cut or tissue effect.

Any suitable cross-section of the flexible cutting element may be provided, where altering the shape, size, and/or configuration of the flexible element may advantageously alter the cutting effect, the stiffness, the sharpness, and/or other properties of the flexible cutting element. It will be appreciated that the illustrated versions are disclosed by way of example only and are not intended to be limiting. Varying the cross-sections of the flexible cutting element along the length thereof may provide advantageous tissue effects and/or may be structurally advantageous.

Figure 25:
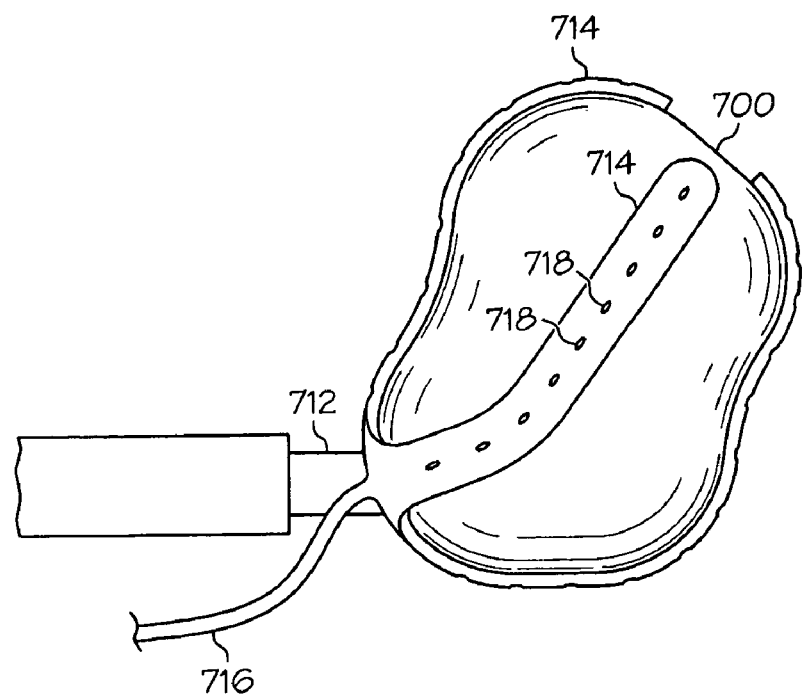
FIG. 25 depicts a perspective side view of a delivery system for an inflatable device.
Figure 26:
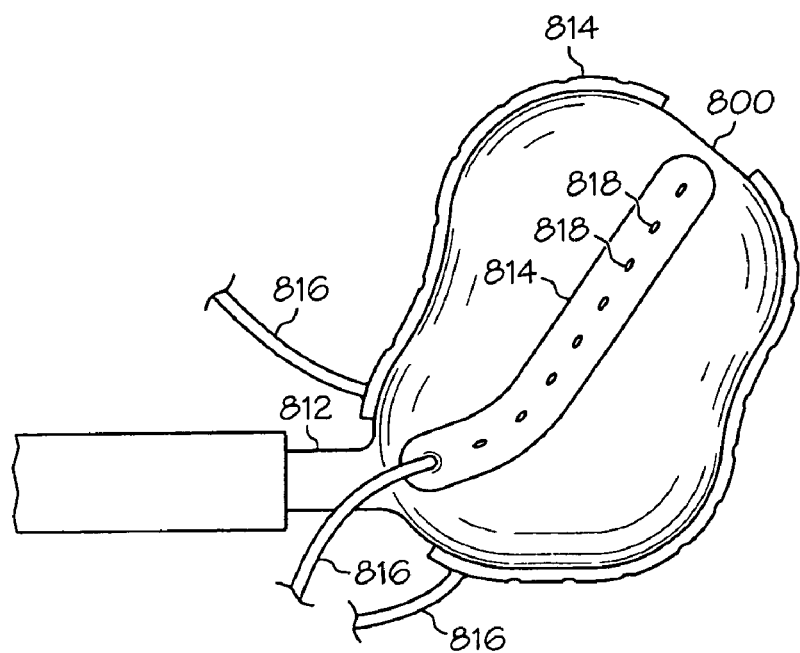
FIG. 26 depicts a perspective side view of an alternative version of a delivery system for an inflatable device.

Referring to FIGS. 25-26, disclosed are alternative versions of an inflatable device, such as may be used with the fracture reduction apparatus (200) shown in FIG. 10, for use in orthopedic procedures directed, for example, towards restoring the anatomy of diseased or fractured bone. Any suitable bone, such as a vertebra, may be prepped by providing a cavity therein in accordance with devices and methods described herein. Pre-existing cavities or pre-formed cavities, such as natural cavities formed within bones, may also be utilized. As has been discussed, an inflatable device, such as a balloon, may then be inserted into the cavity. Once introduced, the inflatable device may be unfolded and/or inflated through the application of air, gas, fluid, a liquid matrix, bone paste, bone cement, bone matrix, or the like, via a lumen fluidly connected thereto. The terms "inflate" and "inflation" shall refer to distention with fluid and/or gas, an increase in volume, swelling, dilation, and/or expansion. The inflatable device may then be inflated intramedullarily with one of a plurality of lumens to apply outward pressure to the interior surface of the fractured bone.

Thus, the versions of inflatable balloons may be particularly useful in minimally invasive surgery and may be used for at least the following specific applications, among others: (1) treatment or prevention of bone fracture, (2) joint fusion, (3) implant fixation, (4) tissue harvesting (especially bone), (5) removal of diseased tissue (hard or soft tissue), (6) general tissue removal (hard or soft tissue), (7) vertebroplasty, and (8) kyphoplasty.

Referring to FIG. 25, an inflatable device (700) is shown having a delivery lumen (712) associated therewith and a plurality of delivery lumen, tubes, tentacles, or projections (714), where the projections (714) are independently filled or inflated from the inflatable device (700) via a delivery lumen (716) and are configured to deliver flowable material, bone cement, or other material, through pores (718), holes, slots, apertures, or the like, therein. In one version, the pores (718) are configured to deliver material to a predetermined location, where multiple apertures and the location of the tentacle help deliver cement in multiple locations at the same time along the anterior surface of the body. In this manner flowable material can be delivered to desirable regions, such as the anterior surface of the body, and can be directed away from less desirable regions such as, for example, the posterior side of the body.

The tentacles or projections (714) may be made of any suitable material such as balloon material, semi-rigid material, short segments of rigid material, tacky material, memory retention material, adhesive material, rigid material, elastomeric material, and/or any other suitable material. The tentacles or projections (714) may be used to deliver any suitable material including the addition of an adhesive, bone matrix, bone paste, bone cement, synthetic paste, therapeutic agent, healing agent, structural agent, or other suitable material, may assist or speed the healing process, assist in fitting the balloon properly, provide a dye or visual marker or the like to visually identify the position of the balloon in a bone through scans or x-ray, provide structural support, or serve any other suitable purpose. Any suitable number of chambers for any suitable purpose are contemplated. Projections (714), tentacles, or the like, may then be pressurized or sized via the associated lumen (716) to a desirable pressure, size, configuration, shape, or the like, for the delivery of a particular material. Any suitable number of projections (714) may be used to deliver material at any suitable location.

Tentacles or projections (714), which include tubes, rigid tubes, semi-rigid tubes, lumens, flexible lumens, bars, spines, protuberances, extensions, support members, combinations thereof, or the like, may be inserted into, attached to, affixed to, coupled with, or formed integrally with the inflatable device (700), such as the fracture reduction apparatus (200) shown in FIG. 10, in a linear configuration, in a non-linear configuration, in an annular configuration, in a lateral configuration, in a longitudinal configuration, in a wave-shaped configuration, in a random configuration, in a non-linear configuration, in a threaded configuration, and/or in any other suitable configuration. The tentacles or projections (714) may be coupled with, for example, the inner or outer surface of the inflatable member. Delivery of materials may be independent of the inflatable device (700) or combined with the inflatable device. The projections (714), or the like, may project in any suitable direction or manner, such as outwardly from the inflatable device or inwardly towards the centroid of the balloon (700).

Additionally, the tentacles or projections (714) may be provided with multiple chambers, cavities, lumens, tubes, or the like configured to perform various functions. The projections may include a porous outer surface that is connected to a delivery lumen, where an adhesive or the like may be administered. Individual projections may be inflatable and may, for example, further include concentric or concatenated chambers.

Referring to FIG. 26, a plurality of tentacles or projections (814) may be used to deliver material, such as bone cement, via one or a plurality of corresponding delivery lumens (816), as illustrated, in conjunction with a balloon (800). In such a manner, different materials may be directed to different projections. A single tentacle or projection (814) may be associated with a single delivery lumen (816), multiple projections (814) may be associated with a single delivery lumen (816), and/or multiple projections (814) may be associated with multiple delivery lumens (816). Multiple delivery lumens (816) may be connected to a single delivery source or to a plurality of delivery sources and may be utilized simultaneously or at different times. In an alternative version, the tentacle may be a sheath, lumen, or tubing that completely or substantially covers the outer surface of the balloon (800) where, for example, the sheath may have apertures that can be pumped out and/or forced out when the sheath is compressed against cortical bone.

The versions presented in this disclosure are examples. Those skilled in the art can develop modifications and variants that do not depart from the spirit and scope of the disclosed cavitation devices and methods. Thus, the scope of the invention should be determined by appended claims and their legal equivalents, rather than by the examples given.

We claim:
1. A cutting apparatus comprising:
(a) a handle;
(b) an insertion tube, the insertion tube being associated with the handle;
(c) an end effector, the end effector being associated with the insertion tube, wherein the end effector further includes:
(i) a body, the body having a proximal portion and a distal portion;
(ii) an aperture formed in the body;
(iii) a transverse member, the transverse member being positioned within the aperture of the body adjacent the distal end of the body;
(iv) a cutting member, the cutting member including an elongated portion having a first end and a second end, wherein the first end of the cutting member is coupled with the proximal portion of the body of the end effector and the elongated portion is wrapped around the transverse member; and
(d) an elongate shaft, the shaft being associated with the second end of the cutting member, wherein the shaft is associated with the cutting member such that distally translating the shaft urges the cutting member outward through the aperture of the end effector and proximally translating the shaft retracts the cutting member into the aperture and against the transverse member.

2. The apparatus of claim 1, wherein the transverse member is selected from the group consisting of a pin, a catch, and a guide.

3. The apparatus of claim 1, wherein the shaft is coupled directly with the second end of the cutting member.

4. The apparatus of claim 1, wherein the cutting member is an elongated member selected from the group consisting of a flexible member, a semi-flexible member, semi-rigid member, a band, a polymer member, a metal member, a shape memory alloy member, a nickel-titanium alloy member, an aluminum member, a carbon steel member, a titanium member, a stainless steel member, and combinations thereof.

5. The apparatus of claim 1, wherein the end effector further comprises a transition member, wherein the transition member couples the shaft with the second end of the cutting member.

6. The apparatus of claim 5, wherein the transition member is guided by a track.

7. The apparatus of claim 5, wherein the transition member is guided by a keyed channel.

8. The apparatus of claim 5, wherein the transition member prevents rotation of the shaft relative to the end effector.

9. The apparatus of claim 1, wherein the cutting member is fully retracted within the aperture of the end effector when the cutting member is pulled taut against the transverse member.

10. The apparatus of claim 1, wherein the end effector is configured to articulate and rotate.

11. The apparatus of claim 1, wherein the first end of the cutting member is curled around the proximal end of the end effector.

12. A cutting apparatus comprising:
   (a) a handle;
   (b) an insertion tube, the insertion tube being associated with the handle;
   (c) an end effector, the end effector being associated with the insertion tube, wherein the end effector further includes:
      (i) a body, the body having a proximal portion and a distal portion;
      (ii) an aperture formed in the body, the aperture having a proximal end and a distal end;
      (iii) a transverse member, the transverse member being positioned within the aperture of the body adjacent the proximal end of the aperture;
      (iv) a cutting member, the cutting member including an elongated portion having a first end and a second end, wherein the first end of the cutting member is coupled with the distal portion of the body of the end effector and the elongated portion is wrapped around the transverse member; and
   (d) an elongate shaft, the shaft being associated with the second end of the cutting member, wherein the shaft is associated with the cutting member such that proximally translating the shaft urges the cutting member outward through the aperture of the end effector and distally translating the shaft retracts the cutting member into the aperture and against the transverse member.

13. The apparatus of claim 12, wherein the transverse member is selected from the group consisting of a pin, a catch, and a guide.

14. The apparatus of claim 12, wherein the shaft is coupled directly with the second end of the cutting member.

15. The apparatus of claim 12, wherein the cutting member is an elongated member selected from the group consisting of a flexible member, a semi-flexible member, semi-rigid member, a band, a polymer member, a metal member, a shape memory alloy member, a nickel-titanium alloy member, an aluminum member, a carbon steel member, a titanium member, a stainless steel member, and combinations thereof.

16. The apparatus of claim 12, wherein the end effector further comprises a transition member, wherein the transition member couples the shaft with the second end of the cutting member.

17. The apparatus of claim 16, wherein the transition member is guided by a track.

18. The apparatus of claim 16, wherein the transition member is guided by a keyed channel.

19. The apparatus of claim 16, wherein the transition member prevents rotation of the shaft relative to the end effector.

20. The apparatus of claim 12, wherein the cutting member is fully retracted within the aperture of the end effector when the cutting member is pulled taut against the transverse member.

21. The apparatus of claim 12, wherein the end effector is configured to articulate and rotate.

* * * * *